(12) United States Patent
Bill

(10) Patent No.: US 9,760,568 B2
(45) Date of Patent: Sep. 12, 2017

(54) ENABLING AN IM USER TO NAVIGATE A VIRTUAL WORLD

(71) Applicant: AOL INC., Dulles, VA (US)

(72) Inventor: David S. Bill, San Francisco, CA (US)

(73) Assignee: Oath Inc., Dulles, VA (US)

( * ) Notice: Subject to any disclaimer, the term of this patent is extended or adjusted under 35 U.S.C. 154(b) by 434 days.

(21) Appl. No.: 14/270,744

(22) Filed: May 6, 2014

(65) Prior Publication Data

US 2014/0330550 A1 Nov. 6, 2014

Related U.S. Application Data

(63) Continuation of application No. 11/850,235, filed on Sep. 5, 2007, now Pat. No. 8,726,195.
(Continued)

(51) Int. Cl.
*G06F 17/28* (2006.01)
*G06Q 10/10* (2012.01)
(Continued)

(52) U.S. Cl.
CPC ........... *G06F 17/289* (2013.01); *G06Q 10/10* (2013.01); *G06T 19/006* (2013.01); *H04L 51/046* (2013.01); *A61B 5/744* (2013.01); *A63F 2300/5553* (2013.01); *A63F 2300/572* (2013.01); *A63F 2300/575* (2013.01); *G06N 3/006* (2013.01); *G06Q 30/02* (2013.01); *G06Q 50/01* (2013.01); *H04N 5/44543* (2013.01);
(Continued)

(58) Field of Classification Search
CPC ........ A63F 2300/5553; A63F 2300/572; A63F 2300/575; G06Q 30/02
See application file for complete search history.

(56) References Cited

U.S. PATENT DOCUMENTS 5,086,394 A 2/1992 Shapira
5,276,905 A 1/1994 Hurst et al.
(Continued)

FOREIGN PATENT DOCUMENTS

WO WO 2005020129 A3 * 1/2008 ............. A63F 13/12

*Primary Examiner* — Jeffery A Gaffin
*Assistant Examiner* — John M Heffington
(74) *Attorney, Agent, or Firm* — Finnegan, Henderson, Farabow, Garrett & Dunner LLP

(57) ABSTRACT

Systems and methods are provided for enabling communications between users of an instant messaging application and a virtual world environment. In accordance with one implementation, a method is provided that includes operations performed by one or more processors, including enabling a first user to navigate the virtual world environment by controlling an avatar representing the first user. The method also includes capturing a first paralinguistic indicator made by the first user, the first paralinguistic indicator configured for communications in the virtual world environment. In addition, the method includes translating the first paralinguistic indicator into a message configured for text-based communications in the instant messaging application, the message comprising at least one of a text description of the first paralinguistic indicator and a second paralinguistic indicator configured for communications in the instant messaging application. The method further includes providing the message to a second user.

20 Claims, 9 Drawing Sheets

Related U.S. Application Data

(60) Provisional application No. 60/864,883, filed on Nov. 8, 2006, provisional application No. 60/824,537, filed on Sep. 5, 2006.

(51) Int. Cl.

| | | |
|---|---|---|
| *G06T 19/00* | (2011.01) | |
| *H04L 12/58* | (2006.01) | |
| *G06Q 50/00* | (2012.01) | |
| *A61B 5/00* | (2006.01) | |
| *H04N 21/4788* | (2011.01) | |
| *H04N 21/84* | (2011.01) | |
| *H04N 21/442* | (2011.01) | |
| *H04N 21/61* | (2011.01) | |
| *H04N 21/6547* | (2011.01) | |
| *H04N 21/658* | (2011.01) | |
| *H04N 5/445* | (2011.01) | |
| *H04N 21/45* | (2011.01) | |
| *H04N 21/258* | (2011.01) | |
| *G06N 3/00* | (2006.01) | |
| *G06Q 30/02* | (2012.01) | |

(52) U.S. Cl.
CPC . *H04N 21/25883* (2013.01); *H04N 21/25891* (2013.01); *H04N 21/44222* (2013.01); *H04N 21/4532* (2013.01); *H04N 21/4788* (2013.01); *H04N 21/6125* (2013.01); *H04N 21/6175* (2013.01); *H04N 21/6547* (2013.01); *H04N 21/6582* (2013.01); *H04N 21/84* (2013.01)

(56) References Cited

U.S. PATENT DOCUMENTS

| | | |
|---|---|---|
| 5,327,486 A | 7/1994 | Wolff et al. |
| 5,533,110 A | 7/1996 | Pinard et al. |
| 5,548,637 A | 8/1996 | Heller et al. |
| 5,557,659 A | 9/1996 | Hyde-Thomson |
| 5,608,786 A | 3/1997 | Gordon |
| 5,721,906 A | 2/1998 | Siefert |
| 5,742,905 A | 4/1998 | Pepe et al. |
| 5,774,670 A | 6/1998 | Montulli |
| 5,793,365 A | 8/1998 | Tang et al. |
| 5,802,470 A | 9/1998 | Gaulke et al. |
| 5,850,594 A | 12/1998 | Cannon et al. |
| 5,867,162 A | 2/1999 | O'Leary et al. |
| 5,870,744 A | 2/1999 | Sprague |
| 5,872,521 A | 2/1999 | Lopatukin et al. |
| 5,878,219 A | 3/1999 | Vance, Jr. et al. |
| 5,880,731 A | 3/1999 | Liles |
| 5,893,091 A | 4/1999 | Hunt et al. |
| 5,893,099 A | 4/1999 | Schreiber et al. |
| 5,920,692 A | 7/1999 | Nguyen et al. |
| 5,940,488 A | 8/1999 | DeGrazia et al. |
| 5,948,058 A | 9/1999 | Kudoh et al. |
| 5,951,643 A | 9/1999 | Shelton et al. |
| 5,951,652 A | 9/1999 | Ingrassia, Jr. et al. |
| 5,954,798 A | 9/1999 | Shelton et al. |
| 5,960,173 A | 9/1999 | Tang et al. |
| 5,987,113 A | 11/1999 | James |
| 5,991,791 A | 11/1999 | Siefert |
| 6,009,413 A | 12/1999 | Webber et al. |
| 6,012,051 A | 1/2000 | Sammon, Jr. et al. |
| 6,014,638 A | 1/2000 | Burge et al. |
| 6,026,403 A | 2/2000 | Siefert |
| 6,026,429 A | 2/2000 | Jones et al. |
| 6,065,047 A | 5/2000 | Carpenter et al. |
| 6,073,138 A | 6/2000 | De l'Etraz et al. |
| 6,081,830 A | 6/2000 | Schindler |
| 6,085,223 A | 7/2000 | Carino, Jr. et al. |
| 6,088,435 A | 7/2000 | Barber et al. |
| 6,151,584 A | 11/2000 | Papierniak et al. |
| 6,161,130 A | 12/2000 | Horvitz et al. |
| 6,166,730 A | 12/2000 | Goode et al. |
| 6,175,831 B1 | 1/2001 | Weinreich et al. |
| 6,199,103 B1 | 3/2001 | Sakaguchi et al. |
| 6,260,148 B1 | 7/2001 | Aggarwal et al. |
| 6,269,369 B1 | 7/2001 | Robertson |
| 6,301,609 B1 | 10/2001 | Aravamudan et al. |
| 6,324,541 B1 | 11/2001 | De l'Etraz et al. |
| 6,330,590 B1 | 12/2001 | Cotten |
| 6,347,332 B1 | 2/2002 | Malet et al. |
| 6,359,622 B1 | 3/2002 | Hayes-Roth |
| 6,374,290 B1 | 4/2002 | Scharber et al. |
| 6,389,127 B1 | 5/2002 | Vardi et al. |
| 6,389,372 B1 | 5/2002 | Glance et al. |
| 6,404,438 B1 | 6/2002 | Hatlelid et al. |
| 6,415,318 B1 | 7/2002 | Aggarwal et al. |
| 6,421,709 B1 | 7/2002 | McCormick et al. |
| 6,425,012 B1 | 7/2002 | Trovato et al. |
| 6,430,604 B1 | 8/2002 | Ogle et al. |
| 6,446,112 B1 | 9/2002 | Bunney et al. |
| 6,449,344 B1 | 9/2002 | Goldfinger et al. |
| 6,507,866 B1 | 1/2003 | Barchi |
| 6,525,747 B1 | 2/2003 | Bezos |
| 6,535,586 B1 | 3/2003 | Cloutier et al. |
| 6,549,937 B1 | 4/2003 | Auerbach et al. |
| 6,571,234 B1 | 5/2003 | Knight et al. |
| 6,584,220 B2 | 6/2003 | Lantrip et al. |
| 6,615,241 B1 | 9/2003 | Miller et al. |
| 6,640,230 B1 | 10/2003 | Alexander et al. |
| 6,677,968 B1 | 1/2004 | Appelman |
| 6,731,308 B1 | 5/2004 | Tang et al. |
| 6,750,881 B1 | 6/2004 | Appelman |
| 6,771,991 B1 | 8/2004 | Gupta et al. |
| 6,788,769 B1 | 9/2004 | Waites |
| 6,800,031 B2 | 10/2004 | Di Cesare |
| 6,801,663 B2 | 10/2004 | Matsushita et al. |
| 6,816,578 B1 | 11/2004 | Kredo |
| 6,876,728 B2 | 4/2005 | Kredo et al. |
| 6,912,563 B1 | 6/2005 | Parker et al. |
| 6,912,564 B1 | 6/2005 | Appelman et al. |
| 6,933,432 B2 | 8/2005 | Shteyn et al. |
| 6,963,839 B1 | 11/2005 | Ostermann |
| 6,987,991 B2 | 1/2006 | Nelson |
| 6,993,532 B1 | 1/2006 | Platt et al. |
| 7,039,676 B1 * | 5/2006 | Day .............. H04M 3/567 |
| | | 345/473 |
| 7,050,109 B2 | 5/2006 | Safadi et al. |
| 7,061,493 B1 | 6/2006 | Cook et al. |
| 7,167,731 B2 | 1/2007 | Nelson |
| 7,174,306 B1 | 2/2007 | Haseltine |
| 7,234,117 B2 | 6/2007 | Zaner et al. |
| 7,359,688 B2 | 4/2008 | Seo et al. |
| 7,379,066 B1 | 5/2008 | Ostermann |
| 7,386,799 B1 | 6/2008 | Clanton et al. |
| 7,395,507 B2 | 7/2008 | Robarts et al. |
| 7,443,283 B2 | 10/2008 | Schmandt et al. |
| 7,447,996 B1 | 11/2008 | Cox et al. |
| 7,463,897 B2 | 12/2008 | Kock |
| 7,496,623 B2 | 2/2009 | Szeto et al. |
| 7,574,332 B2 | 8/2009 | Ballin et al. |
| 7,647,560 B2 * | 1/2010 | Macauley ............... A63F 13/12 |
| | | 709/206 |
| 7,685,237 B1 | 3/2010 | Weaver et al. |
| 7,707,520 B2 | 4/2010 | Ashtekar et al. |
| 7,720,784 B1 * | 5/2010 | Froloff .................. A61B 5/165 |
| | | 600/300 |
| 7,721,216 B2 | 5/2010 | Zaner et al. |
| 7,747,620 B2 * | 6/2010 | Beaupre ............ G06F 17/30766 |
| | | 707/734 |
| 7,778,948 B2 | 8/2010 | Johnson et al. |
| 7,860,705 B2 * | 12/2010 | Afify ..................... G06Q 30/02 |
| | | 704/2 |
| 7,913,176 B1 | 3/2011 | Blattner et al. |
| 8,010,474 B1 | 8/2011 | Bill |
| 8,037,139 B1 * | 10/2011 | Fish ....................... A63F 13/12 |
| | | 709/204 |
| 8,175,929 B2 | 5/2012 | Haseltine |
| 8,214,264 B2 * | 7/2012 | Kasavin ............ G06F 17/30867 |
| | | 705/14.4 |
| 8,473,441 B2 | 6/2013 | Bill |

(56) References Cited

U.S. PATENT DOCUMENTS

| | | | |
|---|---|---|---|
| 8,734,254 B2* | 5/2014 | Aguilar, Jr. | G07F 17/32 463/40 |
| 8,949,899 B2* | 2/2015 | Errico | G06F 17/30035 725/46 |
| 2001/0005861 A1 | 6/2001 | Mousseau et al. | |
| 2002/0007276 A1* | 1/2002 | Rosenblatt | G06Q 30/02 704/260 |
| 2002/0015061 A1 | 2/2002 | Maguire | |
| 2002/0021307 A1 | 2/2002 | Glenn et al. | |
| 2002/0042816 A1 | 4/2002 | Bae | |
| 2002/0049507 A1 | 4/2002 | Hameen-Anttila | |
| 2002/0065894 A1 | 5/2002 | Dalal et al. | |
| 2002/0083060 A1 | 6/2002 | Wang et al. | |
| 2002/0083136 A1 | 6/2002 | Whitten, II | |
| 2002/0091667 A1 | 7/2002 | Jaipuria et al. | |
| 2002/0103801 A1 | 8/2002 | Lysons | |
| 2002/0116463 A1 | 8/2002 | Hart | |
| 2002/0116641 A1 | 8/2002 | Mastrianni | |
| 2002/0130898 A1 | 9/2002 | Ogawa et al. | |
| 2002/0133369 A1 | 9/2002 | Johnson | |
| 2002/0142842 A1* | 10/2002 | Easley | A63F 13/12 463/42 |
| 2002/0160838 A1 | 10/2002 | Kim | |
| 2002/0175953 A1 | 11/2002 | Lin | |
| 2002/0181703 A1 | 12/2002 | Logan et al. | |
| 2002/0184089 A1 | 12/2002 | Tsou et al. | |
| 2002/0188838 A1 | 12/2002 | Welder | |
| 2002/0199095 A1 | 12/2002 | Bandini et al. | |
| 2003/0004855 A1 | 1/2003 | Dutta et al. | |
| 2003/0004872 A1 | 1/2003 | Gardi et al. | |
| 2003/0014407 A1 | 1/2003 | Blatter et al. | |
| 2003/0023875 A1 | 1/2003 | Hursey et al. | |
| 2003/0028524 A1 | 2/2003 | Keskar et al. | |
| 2003/0028595 A1 | 2/2003 | Vogt et al. | |
| 2003/0033420 A1 | 2/2003 | Eyal et al. | |
| 2003/0037112 A1 | 2/2003 | Fitzpatrick et al. | |
| 2003/0040904 A1 | 2/2003 | Whitman et al. | |
| 2003/0043201 A1 | 3/2003 | Abdelhadi et al. | |
| 2003/0050916 A1 | 3/2003 | Ortega et al. | |
| 2003/0060728 A1 | 3/2003 | Mandigo | |
| 2003/0065721 A1 | 4/2003 | Roskind | |
| 2003/0065788 A1 | 4/2003 | Salomaki | |
| 2003/0078919 A1 | 4/2003 | Suzuki et al. | |
| 2003/0105822 A1 | 6/2003 | Gusler et al. | |
| 2003/0108241 A1 | 6/2003 | Colmenarez et al. | |
| 2003/0131061 A1 | 7/2003 | Newton et al. | |
| 2003/0140103 A1 | 7/2003 | Szeto et al. | |
| 2003/0164844 A1 | 9/2003 | Kravitz et al. | |
| 2003/0167324 A1 | 9/2003 | Farnham et al. | |
| 2003/0191816 A1 | 10/2003 | Landress et al. | |
| 2003/0193504 A1 | 10/2003 | Cook et al. | |
| 2003/0196205 A1 | 10/2003 | Chiu et al. | |
| 2003/0210265 A1 | 11/2003 | Haimberg | |
| 2003/0221541 A1 | 12/2003 | Platt | |
| 2003/0233650 A1 | 12/2003 | Zaner et al. | |
| 2003/0236582 A1 | 12/2003 | Zamir et al. | |
| 2004/0002310 A1 | 1/2004 | Herley et al. | |
| 2004/0018858 A1 | 1/2004 | Nelson | |
| 2004/0095359 A1 | 5/2004 | Simon et al. | |
| 2004/0117239 A1 | 6/2004 | Mittal et al. | |
| 2004/0117443 A1 | 6/2004 | Barsness | |
| 2004/0122810 A1 | 6/2004 | Mayer | |
| 2004/0179039 A1 | 9/2004 | Blattner et al. | |
| 2004/0181401 A1 | 9/2004 | Pachet et al. | |
| 2004/0185885 A1 | 9/2004 | Kock | |
| 2004/0189691 A1 | 9/2004 | Jojic et al. | |
| 2004/0215721 A1 | 10/2004 | Szeto et al. | |
| 2004/0235531 A1 | 11/2004 | Anzawa et al. | |
| 2005/0027669 A1 | 2/2005 | Day et al. | |
| 2005/0027839 A1 | 2/2005 | Day et al. | |
| 2005/0050143 A1 | 3/2005 | Guster et al. | |
| 2005/0060377 A1 | 3/2005 | Lo et al. | |
| 2005/0076241 A1 | 4/2005 | Appelman | |
| 2005/0114229 A1 | 5/2005 | Ackley et al. | |
| 2005/0137015 A1* | 6/2005 | Rogers | A63F 13/12 463/42 |
| 2005/0143174 A1* | 6/2005 | Goldman | A63F 13/12 463/42 |
| 2005/0184875 A1 | 8/2005 | Schmandt et al. | |
| 2005/0216529 A1 | 9/2005 | Ashtekar et al. | |
| 2005/0221807 A1 | 10/2005 | Karlsson et al. | |
| 2005/0223328 A1 | 10/2005 | Ashtekar et al. | |
| 2005/0273496 A1 | 12/2005 | Jean et al. | |
| 2006/0075055 A1 | 4/2006 | Littlefield | |
| 2006/0077205 A1 | 4/2006 | Guymon et al. | |
| 2006/0079293 A1 | 4/2006 | Nelson | |
| 2006/0098027 A1 | 5/2006 | Rice et al. | |
| 2006/0123127 A1* | 6/2006 | Littlefield | G06Q 10/107 709/229 |
| 2006/0123351 A1* | 6/2006 | Littlefield | G06F 3/0481 715/768 |
| 2006/0170945 A1 | 8/2006 | Bill | |
| 2007/0002057 A1 | 1/2007 | Danzig et al. | |
| 2007/0021973 A1 | 1/2007 | Stremler | |
| 2007/0050716 A1 | 3/2007 | Leahy et al. | |
| 2007/0064911 A1 | 3/2007 | Bedingfield, Sr. et al. | |
| 2007/0082738 A1 | 4/2007 | Fickie et al. | |
| 2007/0206017 A1 | 9/2007 | Johnson et al. | |
| 2007/0218987 A1 | 9/2007 | Van Luchene et al. | |
| 2007/0233839 A1 | 10/2007 | Gaos | |
| 2007/0239522 A1* | 10/2007 | Kunz | G06Q 30/02 705/14.66 |
| 2007/0239826 A1 | 10/2007 | Ducheneaut et al. | |
| 2007/0240119 A1 | 10/2007 | Ducheneaut et al. | |
| 2007/0255807 A1 | 11/2007 | Hayashi et al. | |
| 2007/0255831 A1 | 11/2007 | Hayashi et al. | |
| 2007/0266090 A1 | 11/2007 | Len | |
| 2007/0288598 A1 | 12/2007 | Edeker et al. | |
| 2008/0059147 A1 | 3/2008 | Afify et al. | |
| 2008/0059570 A1 | 3/2008 | Bill | |
| 2008/0091692 A1 | 4/2008 | Keith et al. | |
| 2008/0163089 A1 | 7/2008 | Altieri | |
| 2008/0208973 A1 | 8/2008 | Hayashi et al. | |
| 2008/0214214 A1 | 9/2008 | Reissmueller et al. | |
| 2008/0215972 A1 | 9/2008 | Zalewski et al. | |
| 2008/0256170 A1 | 10/2008 | Hayashi et al. | |
| 2008/0280684 A1 | 11/2008 | McBride et al. | |
| 2008/0284777 A1 | 11/2008 | Altieri | |
| 2009/0013049 A1 | 1/2009 | Alexander | |
| 2009/0064052 A1 | 3/2009 | Mihalcheon | |
| 2009/0109959 A1 | 4/2009 | Elliott et al. | |
| 2009/0177980 A1 | 7/2009 | Leahy et al. | |
| 2009/0183089 A1 | 7/2009 | Leahy et al. | |
| 2009/0198824 A1 | 8/2009 | Taylor | |
| 2009/0228809 A1 | 9/2009 | Leahy et al. | |
| 2010/0257460 A1 | 10/2010 | Zaner et al. | |
| 2011/0282646 A1 | 11/2011 | Bill | |
| 2013/0274015 A1 | 10/2013 | Bill | |
| 2013/0298044 A1 | 11/2013 | Bill | |

\* cited by examiner

500

| Image | Text String | Text.. | Meaning |
|---|---|---|---|
| | :) :-> | (Nice) | happy |
| | :( | | sad |
| | ;) | | winking |
| | :D | | big grin |
| | ;;) | | batting eyelashes |
| | >:D< | | big hug |
| | :-/ | | confused |
| | :x | | love struck |
| | :"> | | blushing |
| | :P | | tongue |
| | :-* | | kiss |
| | =(( | | broken heart |
| | :-O | | surprise |
| | X( | (mad) | angry |
| | :> | | smug |
| | B-) | | cool |
| | :-S | | worried |
| | #:-S | | whew! |
| | >:) | (devil) | devil |
| | :(( | | crying |
| | :)) | lol | laughing |
| | :\| | | straight face |
| | /:) | | raised eyebrow |
| | =)) | rolf | rolling on the floor |
| | O:) | (angel) | angel |
| | :-B | | nerd |
| | =; | | talk to the hand |

| Sample XML Schema |
|---|
| `<xsd:schema`<br>`xmlns:xsd="http://www.w3.org/2001/XMLSchema">` |
| Negative and forceful |
| `<xsd:enumeration value="anger"/>`<br>`<xsd:enumeration value="annoyance"/>`<br>`<xsd:enumeration value="contempt"/>`<br>`<xsd:enumeration value="disgust"/>`<br>`<xsd:enumeration value="irritation"/>` |
| Negative thoughts |
| `<xsd:enumeration value="doubt"/>`<br>`<xsd:enumeration value="envy"/>`<br>`<xsd:enumeration value="frustration"/>`<br>`<xsd:enumeration value="guilt"/>dai`<br>`<xsd:enumeration value="shame"/>` |
| Negative and passive |
| `<xsd:enumeration value="boredom"/>`<br>`<xsd:enumeration value="despair"/>`<br>`<xsd:enumeration value="disappointment"/>`<br>`<xsd:enumeration value="hurt"/>`<br>`<xsd:enumeration value="sadness"/>` |
| Agitation |
| `<xsd:enumeration value="shock"/>`<br>`<xsd:enumeration value="stress"/>`<br>`<xsd:enumeration value="tension"/>` |
| Positive and lively |
| `<xsd:enumeration value="amusement"/>`<br>`<xsd:enumeration value="delight"/>`<br>`<xsd:enumeration value="elation"/>`<br>`<xsd:enumeration value="excitement"/>`<br>`<xsd:enumeration value="happiness"/>`<br>`<xsd:enumeration value="joy"/>`<br>`<xsd:enumeration value="pleasure"/>` |
| Caring |
| `<xsd:enumeration value="affection"/>`<br>`<xsd:enumeration value="empathy"/>`<br>`<xsd:enumeration value="friendliness"/>`<br>`<xsd:enumeration value="love"/>` |
| Reactive |
| `<xsd:enumeration value="interest"/>`<br>`<xsd:enumeration value="politeness"/>`<br>`<xsd:enumeration value="surprise"/>`<br>`</xsd:schema>` |

- 905a — Negative and forceful
- 905b — Negative thoughts
- 905c — Negative and passive
- 905d — Agitation
- 905e — Positive and lively
- 905f — Caring
- 905g — Reactive

FIG. 9

ENABLING AN IM USER TO NAVIGATE A VIRTUAL WORLD

CROSS-REFERENCE TO RELATED APPLICATION

The present application claims the benefit of priority from U.S. Provisional Application No. 60/864,883, filed Nov. 8, 2006, and entitled "ENABLING AN IM USER TO INTERACT WITH A VIRTUAL WORLD", and from U.S. Provisional Application No. 60/824,537, filed Sep. 5, 2006, and titled "A SYSTEM FOR TRANSLATING PARALINGUISTIC INDICATORS." The contents of the prior applications are incorporated herein by reference in their entirety.

TECHNICAL FIELD

The document relates generally to a system and method for translating paralinguistic indicators.

SUMMARY

In one general sense, a user is enabled to interact with a virtual world environment using an instant messenger application by enabling a user to enter the virtual world environment using the instant messenger application that includes an instant messaging (IM) user interface, generating and managing an avatar to represent the user in the virtual world environment, monitoring a sub-portion of the virtual world environment corresponding to a current location of the user in the virtual world environment, determining descriptions of activities taking place in the sub-portion of the virtual world environment based on the monitoring, and providing the user with the determined descriptions of activities taking place in the sub-portion of the virtual world environment via the IM user interface.

Implementations may include one or more of the following features. For example, providing the user with the descriptions of activities taking place in the sub-portion of the virtual world environment may include providing the user with a textual description of activities taking place in the sub-portion of the virtual world environment. Providing the user with the descriptions of activities taking place in the sub-portion of the virtual world environment may include providing the user with a textual description of at least one of an environment associated with the sub-portion of the virtual world environment, proximity of other users to the user, and activities being performed by other users currently located in the sub-portion of the virtual world environment.

The user may be enabled to provide preference information related to descriptions provided to the user and provided with a description of activities taking place in the sub-portion of the virtual world environment in accordance with the preference information. Enabling the user to provide preference information related to descriptions provided to the user may include enabling the user to provide preference information related to at least one of a volume of descriptions to be provided to the user, a type of descriptions to be provided to the user, and a list of other users about whom descriptions are to be provided to the user.

A collection of descriptions determined to be relevant to the user may be accessed, and the collection of description may be related to a threshold number of descriptions with a number of descriptions determined based on the monitoring. The user may be provided with a sub-set of the descriptions based on relating the collection of description to the threshold number of descriptions. It may be determined that the collection of descriptions exceeds the threshold number of descriptions, and an interest rating may be determined for each of the descriptions in the collection of descriptions. The user may be provided with a sub-set of the descriptions based on the interest ratings.

Providing the user with a sub-set of the descriptions based on the interest rating may include accessing user interest preferences, comparing the interest ratings with the user interest preferences, and identifying descriptions to be included in the sub-set of the descriptions based on the comparison.

A detailed information request may be received from the user regarding a particular description provided to the user, and detailed information related to the particular description may be identified. The user may be provided with detailed information related to the particular description.

BACKGROUND

Users rely on a variety of applications to exchange information with other users.

DESCRIPTION OF FIGURES

FIG. 5 illustrates a table of exemplary emoticons and associated text triggers.

FIG. 9 illustrates an exemplary XML schema for expressing intermediate paralinguistic descriptions.

DETAILED DESCRIPTION

Users of the virtual world systems, such as "Second Life," may wish to communicate paralinguistic indicators (e.g., emotions, gestures, and moods) of their respective avatars to others who utilize text-based communications systems, such as instant messaging or email. However, paralinguistic indicators in virtual world systems may be richer (e.g., capable of displaying complex emotions or gestures) than paralinguistic indicators available in text-based communications systems. Consequently, paralinguistic indicators used in virtual world systems may not be compatible with paralinguistic indicators used in text-based communication systems.

For illustrative purposes, FIGS. 1-9 illustrate aspects (e.g., user interface, process flow, system diagram) related to a system for translating paralinguistic indicators at a paralinguistic translation server. A user of a virtual world (VW) system, who operates an avatar inside the virtual world, communicates with a user of an instant messaging (IM) system. For example, the VW user may wish to express a set of emotions or actions through the behavior of an avatar and have these emotions/actions communicated to the IM user.

Thus, if the VW user is feeling angry, the VW user may communicate an angry mood through some actions of her avatar. Consequently, paralinguistic indicators of the VW user's avatar (e.g., gesticulations, actions, or facial expressions) are encoded as a set of data and transmitted from the VW system to the paralinguistic translation server. The paralinguistic translation server translates paralinguistic indicators of the VW system into the paralinguistic indicators of the IM system. For example, the paralinguistic translation server evaluates the avatar's paralinguistic indicators and translates these indicators into the at least partially synonymous or corresponding paralinguistic indicator(s) in the IM system. The paralinguistic indicators are then added to an instant message and transmitted to the IM user. The paralinguistic indicators in the IM system may be still indicators, such as an "angry face" emoticon, or more complex, animated indicators, such as expressions conveyed by an animated SuperBuddy®. The paralinguistic indicator(s) may be two-dimensional or three-dimensional.

Figure 1:
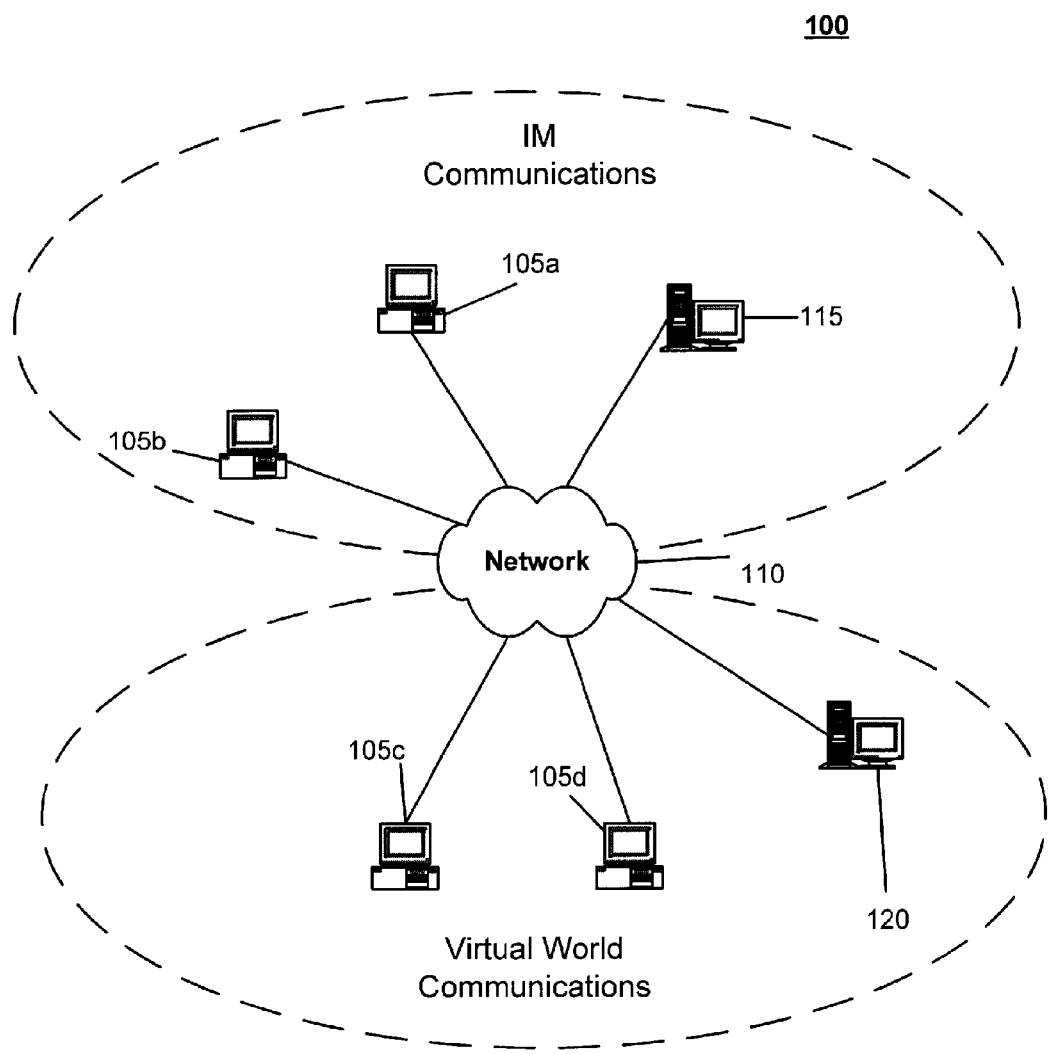
FIG. 1 illustrates an exemplary network computing environment enabling communications between users of instant messaging clients and virtual world clients.

FIG. 1 illustrates an exemplary networked computing environment 100 enabling communications between users of instant messaging (IM) clients and virtual worlds (VWs) clients. A network 110 interconnects client systems 105a-105d, which connect to network 110 through various communication mediums, such as a modem connected to a telephone line (using, for example, serial line internet protocol (SLIP) or point-to-point protocol (PPP)) or a direct internetwork connection (using, for example, transmission control protocol/internet protocol (TCP/IP)). As such, users who are distributed geographically communicate using client systems 105a-105d. For example, users operating client systems 105a and 105b are utilizing instant IM clients to communicate with each other and virtual world users operating client systems 105c-105d. Similarly, users operating client systems 105c-105d are communicating within a virtual world and also with users outside of a virtual world. A virtual world presents an interactive three-dimensional (3D) graphical scene to users operating client systems 105c-105d, such that users operating client systems 105c-105d may interact via network 110 with the world and each other through textual, audio, and/or graphical communications.

Each of the client systems 105a-105d may be implemented using, for example, a general-purpose computer capable of responding to and executing instructions in a defined manner, a personal computer, a special-purpose computer, a workstation, a server, a device, a component, or other equipment or some combination thereof capable of responding to and executing instructions. Client systems 105a-105d may receive instructions from, for example, a software application, a client, a piece of code, a device, a computer, a computer system, or a combination thereof, which independently or collectively direct operations, as described herein. These instructions may take the form of one or more communications clients that facilitate communications between the users of client systems 105a-105d. For instance, such communications clients may include electronic mail (e-mail) clients, IM clients, virtual world clients, or voice-over-IP clients. The instructions may be embodied permanently or temporarily in any type of machine, component, equipment, storage medium, or propagated signal that is capable of being delivered to the client systems 105a-105d.

Client systems 105a-105d include a communications interface (not shown) used by the communications clients to send communications through network 110. The communications may include e-mail, audio data, video data, general binary data, or text data (e.g., data encoded in American Standard Code for Information Interchange (ASCII) format).

The network 110 typically includes a communications infrastructure facilitating communications between the different client systems, and may include one or more hosts. Examples of the network 110 include the Internet, Wide Area Networks (WANs), Local Area Networks (LANs), analog or digital wired and wireless telephone networks (e.g., a Public Switched Telephone Network (PSTN)), an integrated Services Digital Network (ISDN), or a Digital Subscriber Line (xDSL), or any other wired or wireless network. The network 110 may include multiple networks or subnetworks, each of which may include, for example, a wired or wireless data pathway.

Computing environment 100 also includes an instant messaging (IM) server 115 and a virtual world (VW) server 120 that are connected to network 110. The IM server 115 and the VW server 120 are used to facilitate direct or indirect communications between the client systems 105a-105d. As with the client systems 105a-105d, the IM server 115 and the VW server 120 may be implemented using, for example, a general-purpose computer capable of responding to and executing instructions in a defined manner, a personal computer, a special-purpose computer, a workstation, a server, a device, a component, or other equipment or some combination thereof capable of responding to and executing instructions. The IM server 115 and the VW server 120 may receive instructions from, for example, a software application, a client, a piece of code, a device, a computer, a computer system, or a combination thereof, which independently or collectively direct operations, as described herein. These instructions may take the form of one or more communications clients. Such communications clients may include, for example, e-mail clients, VW clients, IM clients, and voice-over-IP clients. The instructions may be embodied permanently or temporarily in any type of machine, component, equipment, storage medium, or propagated signal that is capable of being delivered to the IM server 115 and the VW server 120.

Further, the IM server 115 and the VW server 120 include communications interfaces (not shown) used by the communications clients to exchange communications through network 110. The communications may include different forms of data, such as e-mail data, audio data, video data, general binary data, or text data.

Figure 2:
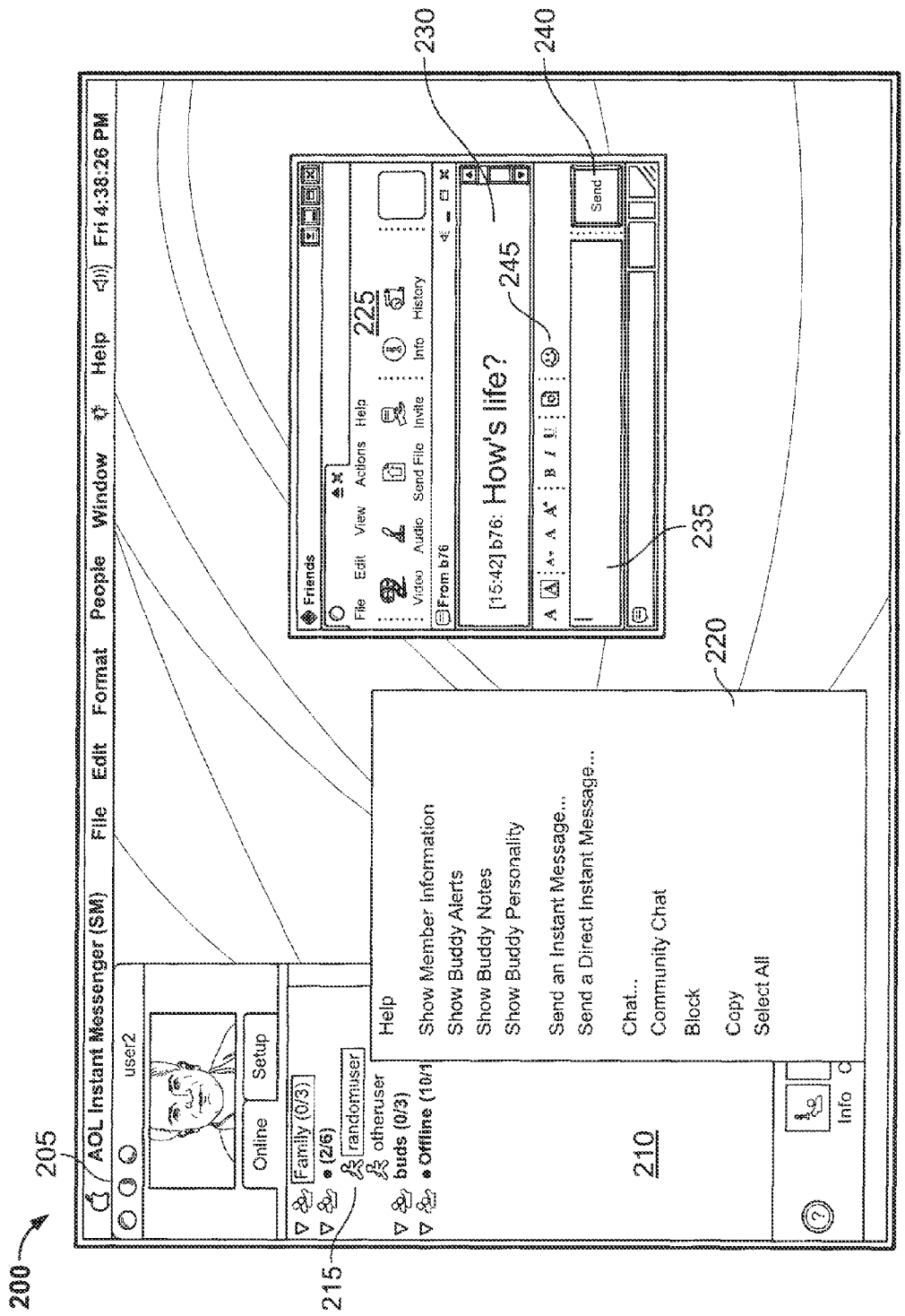
FIG. 2 illustrates an exemplary instant messaging interface presented to a user of an IM client.

FIG. 2 illustrates an exemplary instant messaging interface presented to a user of one of the client systems, such as the client system 105a. The IM client enables a user to communicate in real-time with other users using text and other input. For example, the IM client enables the user to send text communications in an instant message, transfer files, and communicate using voice. Examples of IM clients include those provided by AOL (America Online's AOL Instant Messenger (AIM)), Yahoo Messenger, MSN Messenger, and ICQ.

As shown, the IM system 200 presents a user with an IM user interface 205. User interface 205 includes a text box 210 that displays representations 215 of the user's contacts (e.g., an AIM Buddy appearing in an AIM Buddy List™, which are other users participating in an IM system, by executing an IM client on another client system. For instance, in the exemplary interface shown, there are representations for two contacts, "randomuser" and "otheruser." The representations 215 provide status information for the user about the contact, such as whether the contact is online, how long the contact has been online, whether the contact is away, or whether the contact is using a mobile device.

The list of contacts displayed in text box 210 of user interface 205 may be referred to as a list of co-users, and the IM client user may add or remove contacts from the contact list. In the example shown, the representations 215 are rendered as icons showing the screen names of the contacts.

The IM clients may use the IM server 115 to assist in communications between users of the IM clients. The IM server 115 may be configured to interact with a different IM services irrespective of which IM client is being used. The IM server 115 also may support associated services, such as administrative matters, advertising, directory services, chat, and interest groups related to instant messages.

To facilitate the transfer of data, the IM server 115 may implement one or more standard or proprietary IM protocols. The one or more protocols may enable the IM server 115 to facilitate the establishment of a peer-to-peer communication session between the IM client clients, or assist IM communications by directly routing communications between the IM client clients.

To engage in IM communications when using an IM server 115, an IM client on one of client systems 105a-105d establishes a connection with the IM server 115, authenticating itself in the process. Once the client has been authenticated, the IM client indicates whether a particular contact is presently online, exchanging IMs with particular contacts, participating in a group chat room, or trading files, such as pictures, invitations or documents. The IM client also may refresh other information such as an indication of (or ability to search for) other users with similar interests, and customized information such as news and stock quotes, and search the World Wide Web.

When a contact is online, the user may communicate or interact with the contact in a number of ways. For instance, the user can send an instant message to the contact (typically in the form of text). Sending a message opens up a window 225 in which messages can be typed and viewed as they are communicated back-and-forth between the user and the contact. Window 225 includes a text box 230 and an edit box 235. The sent and received messages of the user are displayed in text box 230. The sender's (i.e., user's or contact's) screen name may be listed beside the sender's corresponding message in text box 230. For instance, in the exemplary window shown, the user (whose screen name is "randomuser") has received a message "How's life?" from the contact (whose screen name is "b76"). To send a reply message, the user types the message in edit box 235 and activates a send command, for example, by pressing an ENTER key or selecting on a Send icon 240. In addition, an emoticon link 235 may be selected from window 225 to display a tool for specifying emoticons that are available when communicating with the contact. Generally, emoticons are two-dimensional images that are sent when certain triggers are included in the text of an instant message, as will be further discusses with respect to FIG. 5. For example, the character sequence ;) may be displayed as a "winking" smiley face. As a result of entering an emoticon, the entered text, along with the emoticons, is displayed in text box 230 within contact's user interface.

Figure 3:
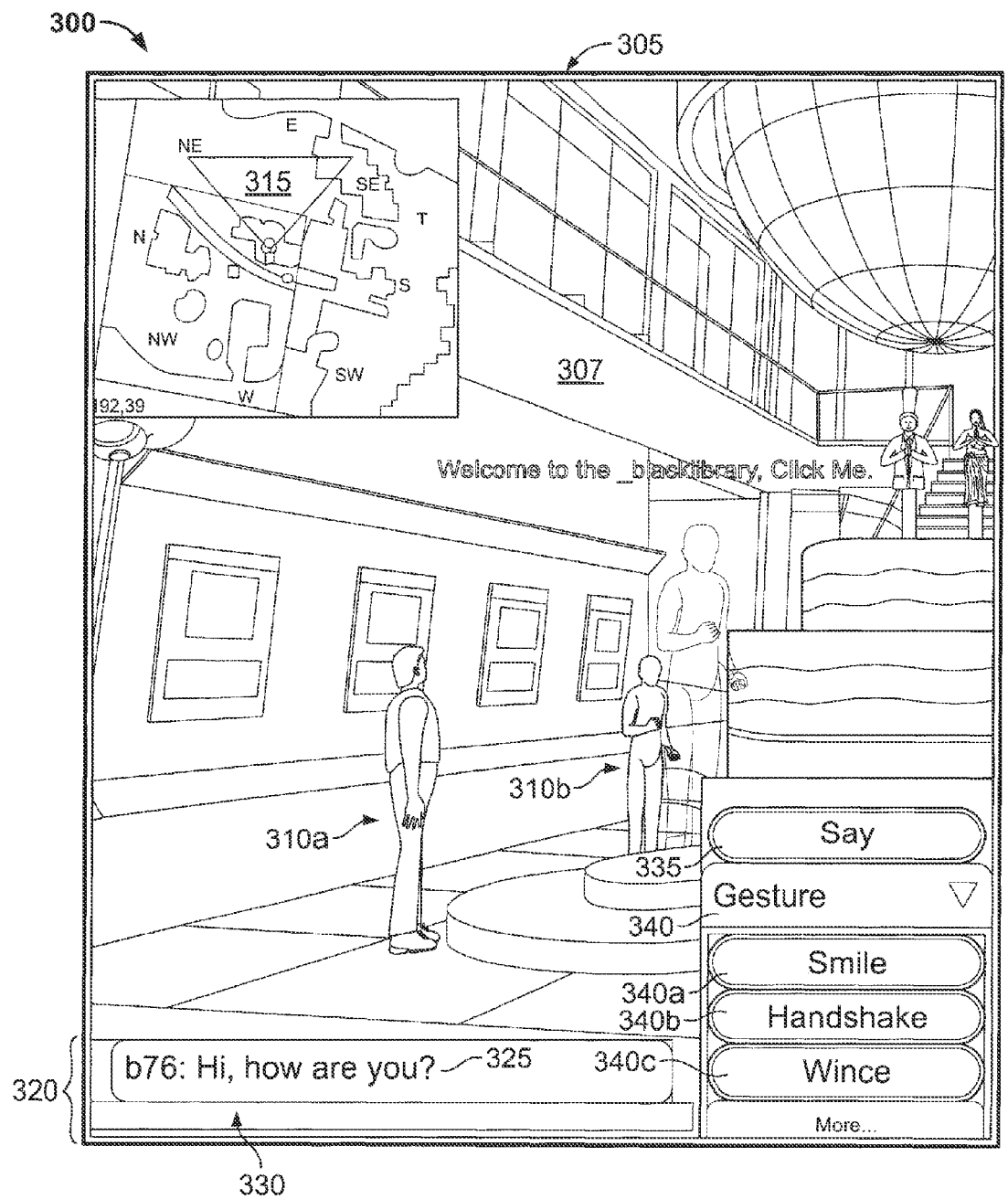
FIG. 3 illustrates an exemplary virtual world interface.

In addition to instant messaging, users of a network computing environment 100 may interact with each other inside a virtual world (VW) environment. FIG. 3 illustrates an exemplary virtual world interface presented to users of the virtual world environment, such as users operating client systems 105c-105d of FIG. 1. Users operating client systems 105c-105d may interact in shared, three-dimensional virtual world through their respective avatars 310a-310b, which are graphical representations of users in the virtual world system 300. Users operating client systems 105c-105d control their avatars through an interface of a VW client 305. For example, the interface 305 enables users to cause their respective avatars 310a-310b to travel around, gesticulate, or communicate with other avatars within the virtual world via text messages, voice, or movements. In addition, VW users may direct their avatars 310a-310b to interact with the 3D graphical scene in the virtual world by creating, moving, or touching various objects and scene elements. Examples of VW clients include "Second Life" by Linden Research, Inc, and "Virtual Worlds" by Microsoft.

As shown, a virtual world system 300 presents a user with a VW client interface 305. User interface 305 has a graphical view box 307, which displays the 3D scene of the virtual world from a point of view of the user's avatar. In addition, user interface 305 has a high-level, topological map of the virtual world 315, which may show users operating client systems 105c-105d the current location of their avatar on the overall map of the virtual world and also may allow users operating client systems 105c-105d to quickly zoom in to the specific locations within the virtual world.

VW users operating client systems 105c-105d can communicate or interact with the virtual world in a number of ways. For instance, the user operating client system 105c can send a message to the user operating client system 105d (typically in the form of text). Sending a message is done by typing the message in a messaging window 320. The messages may be perceived as the messages are exchanged. Messaging window 320 includes a text box 325 and an edit box 330. For example, the sent and received messages of the user operating client system 105c are displayed in text box 325. A user's screen name may be listed beside the avatar's corresponding message in text box 325. For instance, in the exemplary window shown, the user operating client system 105c has received a message "Hi, how are you?" from the user operating client system 105d (whose screen name is "b76"). To send a reply message, the user operating client system 105c types the message in edit box 330 and activates a send command by, for example, pressing an ENTER key.

Users also speak to each other and other users by using voice communications. For example, the user operating client system 105c may press a "Say" button 335 and begin a voice communications session with the user operating client system 105d. In addition, users operating client systems 105c-105d may cause their avatars 310a-310b to gesticulate to each other and other avatars by selecting from a variety of gestures from a pull-down menu 340. Selecting a gesture from the pull-down menu 340 causes user's avatar to perform a specific action in the virtual world. For example, the user operating client system 105c may select a "smile" gesture 340a from a list of available gestures 340, which will cause user's avatar 310a to smile. The actual number of available gestures or gesture combinations may be quite large. Users operating client systems 105c-105d may be able to cause their avatars to express a wide range of emotions, such as happiness, anger, or tiredness, by selecting from a variety of available gestures. For instance, the user operating client system 105c may cause avatar 310a to wince in pain and rub its belly to indicate a stomachache to the user operating client system 105d. In addition, a user may customize the expressions presented by their avatar. For example, the avatar may modify a profile to configure certain facial configurations to be associated with a specified trigger and/or mood. Alternatively or in addition, the user may specify an intensity of emotion that lies within an intensity spectrum. For example, a user may interact with a control mechanism numbered from 0 until 1000, where 0 represents a neutral mood, 100 represents a perturbed mood, 200 represents being upset, up until a value of 1000 (representing extreme anger). Each of the numbers may represent a setting for a facial expression (e.g., an intensity of a facial expression such as a furrowed brow). In the case where the furrowed brow reflects the mood, a first "range of motion" to a first position may represent progressive moods from 0-100 while a second "range of motion" may represent more extreme moods to a second position.

In yet another example, users operating client systems 105c-105d may control their avatars through the use of video with face/gesture/mood tracking software. For example, users operating client systems 105c-105d may configure a desktop video camera to track user actions and expressions in the real world and translate these actions to the avatar actions or moods in the virtual world. Thus, for example, when the user operating client system 105c smiles and waives his hand in front of the webcam, the face/gesture/mood tracking software will detect these actions of the user operating client system 105c and cause his avatar to smile and waive a hand in the virtual world.

For mood tracking, users operating client systems 105c-105d may utilize mood tracking techniques described in U.S. application Ser. No. 11/321,063, filed on Dec. 30, 2005, entitled "Mood-based organization and display of instant messenger buddy lists," the entire contents of which are hereby incorporated by reference. For example, users may train a mood tracking software for better mood recognition. To illustrate a training system, a mood tracking software may capture a user's facial image and analyze the user's facial expression as a baseline indicative of the user's mood. The mood tracking software may then present the user with a predicted image/mood indicator. The mood tracking system then may ask the user if the presented image/mood indicator is indicative of the mood felt by the user. Moreover, if the image/mood indicator is not indicative of expressed mood, the user may advance through a series of images captured during the training session to identify an image associated with the indicated mood. Another example used separately or addition to previously described examples allows a user to identify one or more components in a facial expression indicative of the desired mood (e.g., by allowing the user to highlight a brow structure, a lip structure such as a smile, or an existence of wrinkles in a particular portion). The above examples are only exemplarily and other techniques described in U.S. application Ser. No. 11/321,063 may be used for mood recognition.

The VW clients may use a virtual world server 120 to assist in communications between users of the VW clients. The VW server 120 may support VW services irrespective of a client user's network or Internet access. Thus, for example, VW server 120 may allow users to communicate with other users, regardless of whether they have access to any particular Internet service provider (ISP). The VW server 120 also may support associated services, such as billing, administrative matters, advertising, and directory services related to the virtual world.

To facilitate the transfer of data, the VW server 120 employs one or more standard or proprietary VW communication protocols. The one or more protocols may enable the VW server 120 to facilitate the establishment of a peer-to-peer communication session between the VW client clients, or assist VW communications by directly routing communications between the VW client clients.

To engage in VW communications when using the VW server 120, a VW client running on one of client systems 105c-105d establishes a connection with the VW server 120 and authenticates. Once authenticated, VW users operating client systems 105c-105d may use the VW client to create or modify their avatars 310a-310b, communicate with other VW users through avatars 310a-310b, or interact with the environment of the virtual world through avatars 310a-310b. For example, the user operating client system 105c, may build a "virtual" object, such as a house, and rent this house to the user operating client system 105d for a fee. Then, the avatar 310b of the VW user operating client system 105d is able to inhabit the newly-built house and interact with the objects stored in the house.

VW users operating client systems 105e-105d may communicate with the users outside of the virtual world, such as IM users 105a-105b. This communications may be accomplished by sending instant messages between VW users operating client systems 105c-105d and IM users 105a-105b. Such communications may be either unidirectional or bidirectional—that is, VW users may send messages to IM users and/or IM users may send messages to VW users. Alternatively or in addition, such communications may include email, instant messages, voice communications, chat communications, voice-over-IP, or other communications.

Figure 4:
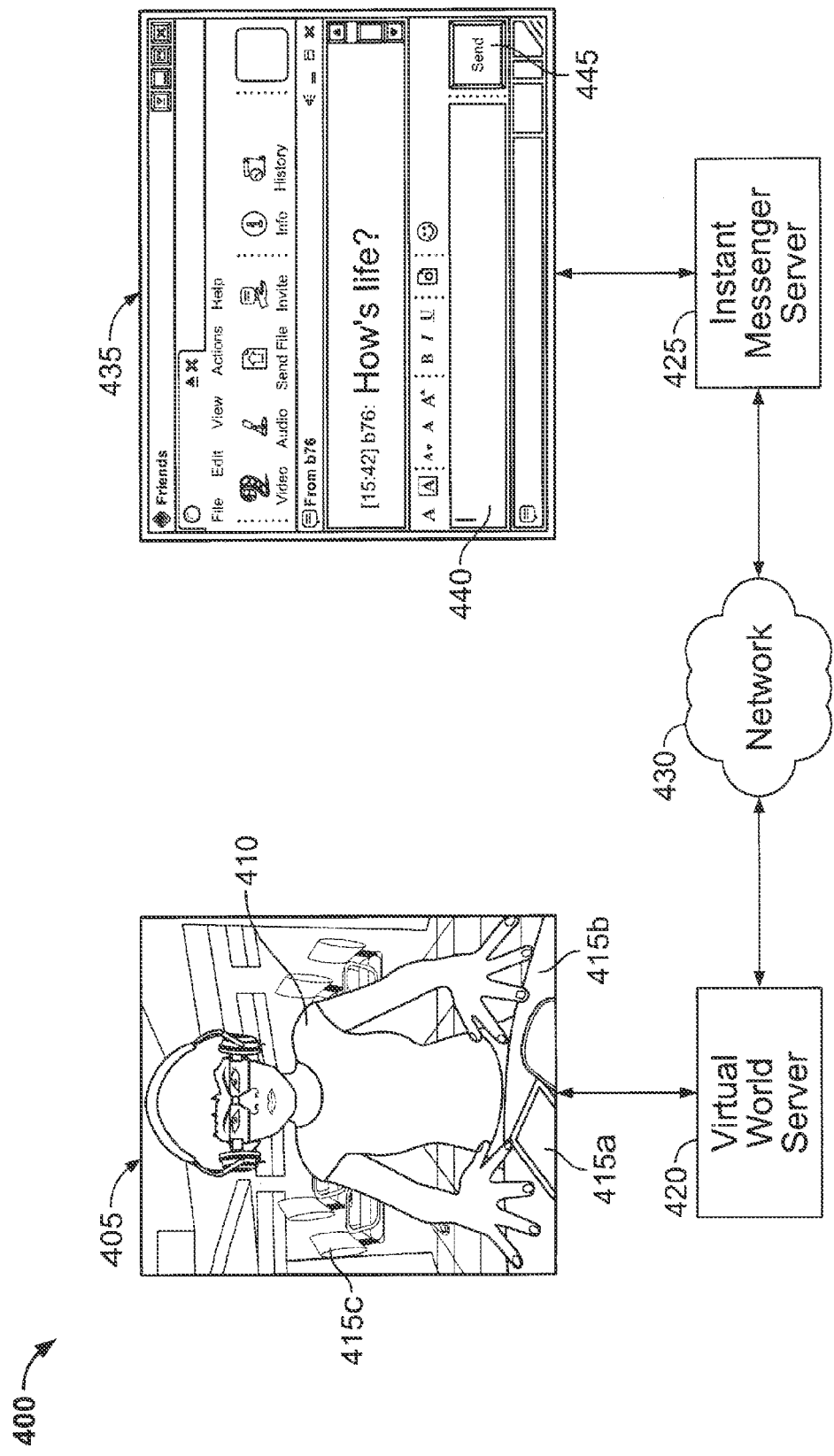
FIG. 4 illustrates communications between an instant messaging system and a virtual world system.

For example, FIG. 4 illustrates communications between an IM system 200 and a virtual world system 300. The VW user operating client system 105c may interact with the virtual world through a user interface of the VW client 405, which is similar to the previously discussed interface 305. The user operating client system 105c is represented in the virtual world by her avatar 410. As described with respect to FIG. 3, actions of the avatar 410 are controlled by the user operating client system 105c through the interface of the VW client 405. Here, for example, user operating client system 105c has directed her avatar 410 to read a book in a virtual library. Hence, avatar 410 is surrounded by a rich graphical environment representative, which includes books 415a, tables 415b, and chairs 415c. Avatar 410 may interact with any of these and other virtual objects.

The user operating client system 105c may wish to communicate with the IM user 105a. In this case, she sends a message from the VW interface 405 to the IM client of the IM user 105a. For instance, in the exemplary window shown, the VW user operating client system 105c (whose screen name is "b76") has sent a message "How is life?" to the IM user 105a. The sent message passes from the VW server 420 to the IM server 425 by way of the network 430, all of which have been described previously with respect to FIG. 1. The message is displayed to the IM user 105a through an interface 435 of the IM client, which has also been described previously with respect to FIG. 1. To send a reply message to the VW user operating client system 105c, the IM user 105a may type the message in edit box 440 and press an ENTER key or click on a Send icon 445.

Communications between the virtual world and text-based clients, such as instant messaging or email, may suffer in at least one respect. The range of avatar emotions, gestures, or moods displayed in a graphical virtual world system may be much "richer" than a similar range of emotions available in a text-based system. In a virtual world, users may be able to express a wide range of their emotions or moods, such as happiness, anger, or tiredness, by choosing a variety of non-verbal indicators for their avatars, including gestures, actions, or facial or body expressions. These indicators, known as paralinguistic indicators, describe the non-verbal elements of communication used to modify meaning and convey emotion. Thus, in the virtual world communications, paralinguistic elements may be expressed by the avatar's facial expressions, gestures, and/or interactions with the surrounding virtual environment.

Similarly, in the text-based communications users have traditionally conveyed their emotions by placing specific paralinguistic indicators within email, chartroom, or instant messages. However, in contrast to the virtual world communications, the paralinguistic indicators in the text-based communications may be more constrained in their scope and expressiveness. For example, text-based paralinguistic elements may be displayed by emoticons, font or color choices, capitalization and the use of non-alphabetic or abstract characters. In particular, emoticons are two-dimensional non-animated images (and sometimes non-animated) that are sent when certain triggers are included in the text of an email, a chat room message, or an instant message. A trigger may include any letter, number, or symbol that may be typed or otherwise entered using a keyboard or keypad. For example, a user may indicate her mood by sending a "smiley face" emoticon by including a ":-)" trigger in the message. In another example, a user may indicate that the user is shouting by capitalizing a message.

Referring to FIG. 5, a table 500 of text-based triggers associated with the commonly used emoticons 505 is shown. Each of the emoticons 505 has multiple associated triggers 510 or 515 which convey a specific meaning 517. More particularly, by way of example, the emoticon 520a, in which the avatar is made to smile, has associated triggers 520b-520c. Each of the triggers 520 includes multiple character strings. In particular, triggers may be include "sideways" expression triggers 520a, such as ":)" and ":-)", and English words, such as a "Nice" trigger 520b. Other examples of a trigger include a particular abbreviation, such as "lol," and an English phrase, such as "Oh no." As discussed previously, when one of the triggers is included in an instant message, the corresponding emoticon is sent in that instant message. In one example, when "Nice" is included in an instant message, the smiling emoticon is sent. In another example, when a user includes a ":P" text trigger in the instant message, a two-dimensional image of a smiley sticking a tongue out is sent to a recipient of the instant message.

When the VW user operating client system 105c communicates with the IM user 105a, paralinguistic indicators used in the virtual world (e.g., gesticulations, actions, facial expressions) are translated to the paralinguistic indicators used in the IM communications using, for example, emoticons or a description of the avatar in the VW. Similarly, paralinguistic indicators included in the communications from the IM user 105a to the VW user operating client system 105c also may be translated.

The translated paralinguistic indicators need to be at least partially synonymous to the original paralinguistic indicators. In other words, the content of non-verbal communications associated with a translated indicator should reflect, correspond to, be related to, or be supported by the content of non-verbal communications associated with the original indicator. Thus, for example, a paralinguistic indicator of "happiness" in the VW should be translated to a similar (although not necessarily identical) indicator in the IM system, such as a large smiley or a happy face. And while a degree of translation between indicators may vary, some correlation between the original and the translated indicators should exist. Therefore, an indicator of "happiness" should not be translated to an indicator that carries a meaning that is entirely unrelated to the original meaning, such as "sleepiness" or "angry."

Figure 6:
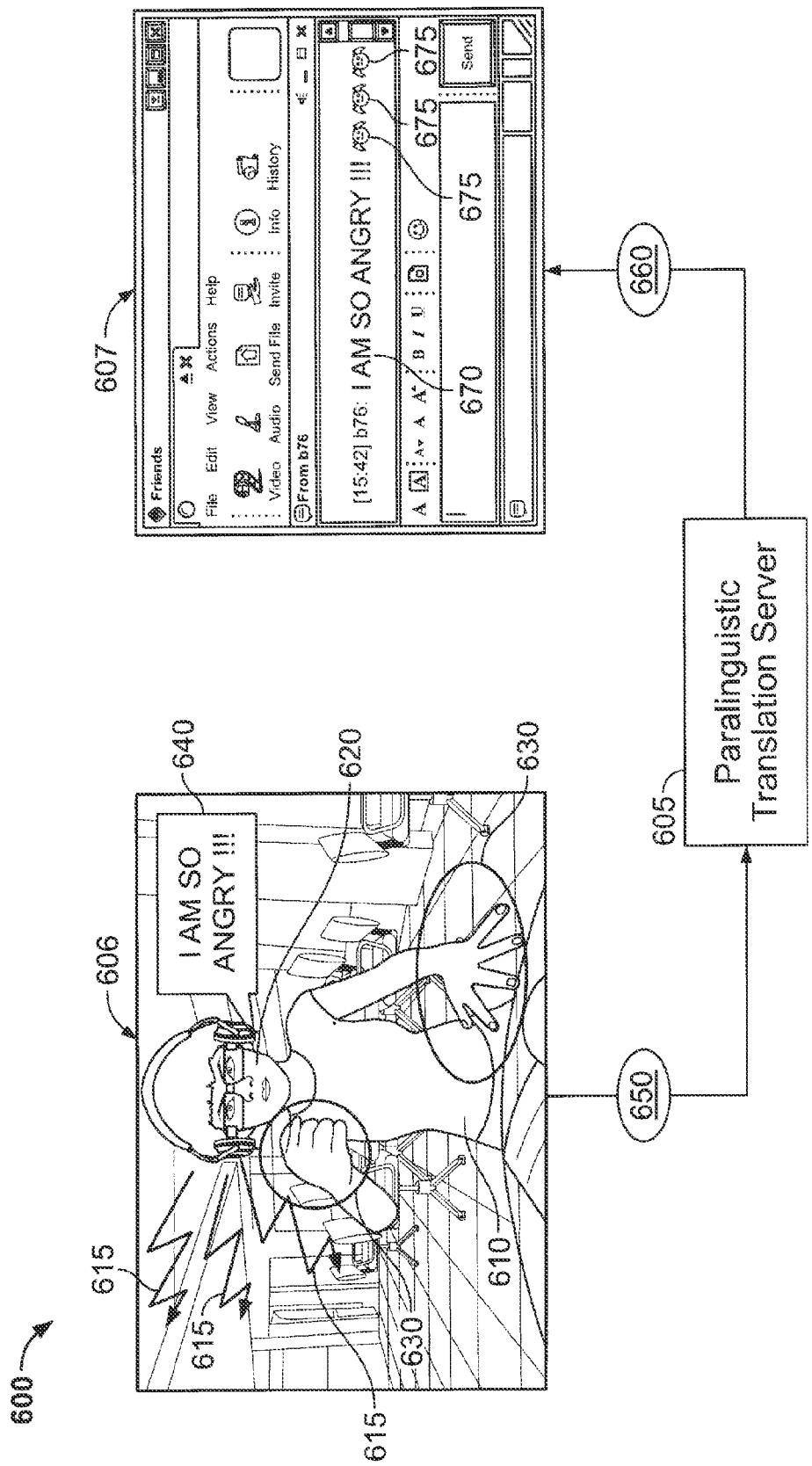
FIG. 6 illustrates a translation of paralinguistic indicators during communications between instant messaging system and a virtual world system.

FIG. 6 illustrates a system for translating paralinguistic indicators at a paralinguistic translation server 605. A user of a virtual world (VW) system 606 (previously described with respect to FIG. 3) is communicating with a user of an IM system 607 (as was previously described with respect to FIG. 2). The VW user operates an avatar 610 inside the virtual world. At some point, the VW user may wish to express a set of emotions or actions through the behavior of avatar 610 and have these emotions/actions communicated to the IM user. For example, if the VW user is feeling angry, the VW user may communicate an angry mood through actions of her avatar 610. The VW user may express her "virtual emotions" in a variety of ways. For instance, the VW user may indicate her anger by displaying the lighting bolts 615 around her avatar's face. In addition, a facial expression 620 of the avatar 610 and specific gesticulations, such as banging fists on the table 630, also may indicate an angry mood. Alternatively or in addition, the VW user may send a text message through the message window 640, where the contents, fonts, or colors of the text message itself may indicate a specific mood. For example, capitalization or very large fonts may indicate screaming. In yet another example, certain emotionally-charged words, such as "happy" or "angry", may indicate the communicated emotions when they appear in the text message. The VW user also may utilize voice communications to communicate with the IM user. In that case, the actual content of the voice communications as well as audio qualities of the voice communications, such as volume or pitch, may be analyzed to determine the emotions/moods. The above indicators of emotions/moods are only exemplary. Other paralinguistic indications of moods/emotions may be used and also may depend on the specific environment of the virtual world system and the desires of the VW user.

The paralinguistic indicators are encoded as a set of data and transmitted from the VW system 606 to the paralinguistic translation server 605 (650). The set of data may be encoded in a binary format or in a markup language, such as HTML or XML. In one XML-based example below, the paralinguistic indicators describe some of the paralinguistic indicators of the user's avatar:

```
<avatar version="1.0">
<?xml version="1.0" encoding="US-ASCII" standalone="yes"?>
    <body body_region="complete" width="512" height="512"
        <body_part name="hair"
            hair_color = "brown"
            texture = "curly"
            length = "long"
        </body_part>
        <body_part name="face"
            color = "green"
            texture = "rugged"
            mood = "agitated"
            expression = "angry"
        </body_part>
    </body>
</avatar>
```

The set of data specifying the paralinguistic indicators within the VW system 606 is received at the paralinguistic translation server 605. Subsequently, the paralinguistic translation server 605 translates paralinguistic indicators of the VW system 606 into the paralinguistic indicators of the IM system 607, such that the translated paralinguistic indicators of the IM system 607 are at least partially synonymous to the received paralinguistic indicators of the VW system 606. Therefore, the translated paralinguistic indicators reflect the content of the received paralinguistic indicators of the VW system 606. The translated paralinguistic indicators may reflect a robust set of content or just partial content, depending on a degree of translation.

In this example, the paralinguistic translation server 605 receives the set of data related to the avatar's mood in the VW system 606. The paralinguistic translation server 605 may evaluate the avatar's angry face 610, the lightning bolts surrounding the avatar 615, the hand gestures 630*a*-630*b*, or the actual content and capitalization of the message 640 ("I AM SO ANGRY!!!), and translate the virtual world's paralinguistic indicators into the synonymous paralinguistic indicator in the IM system 607, such as an "angry bat" emoticon.

The translated emoticon is converted to a set of data related to the paralinguistic indicator in the IM system 607. For example, the paralinguistic translation server may encode the "angry bat" emoticon in such a combination of text triggers that would cause the IM system 607 to display the "angry bat" emoticon on the IM interface 670 when the instant message is received at the IM system 607.

Finally, the paralinguistic translation server transmits the set of data related to the translated paralinguistic indicator (e.g., "angry bat") to the IM system 607 (660). For example, the text triggers related to the "angry bat" emoticon are transmitted along with the text of the instant message to the IM user. When the IM user receives the instant message from the VW user, the IM user sees not only the text of the IM, but also the emoticons 675 displayed by the IM client. These emoticons are at least partially synonymous to the paralinguistic indicators (e.g., emotions, moods, actions, etc) of the VW user's avatar in the virtual world.

The above example demonstrated translation of paralinguistic indicators from the virtual world system to the instant messaging system. Additionally or alternatively, a similar translation may be used to translate communications from the IM system 607 to the VW system 606. For example, the user of the IM system 607 may type a message that includes some paralinguistic indicators, such as smiley faces. The instant message is then transmitted to the user of the VW system 606. In the course of processing the message, the paralinguistic indicators in the instant message are translated at the paralinguistic translation server 605 so that the VW user, in response to receiving an instant message from the IM user, may observe the translated paralinguistic indicators in the virtual world environment. For instance, if the IM user is represented by an avatar in the virtual world, the avatar displays emotions/actions that are at least partially synonymous to the meaning of the paralinguistic indicator in the instant message. Thus, if the IM user transmits a winking emoticon (";-)") to the VW user, the avatar for the IM user also may wink in the virtual world. In addition to the previously-described paralinguistic indicators, the IM user also may provide a variety of textual commands to control the behavior of his avatar in the virtual worlds. For instance, a user may type "lol," "ROFL" or <bang fists>, or <take 3 steps> or other combination of text-triggers/commands to cause his avatar to perform at least partially synonymous actions in the virtual world.

Figure 7:
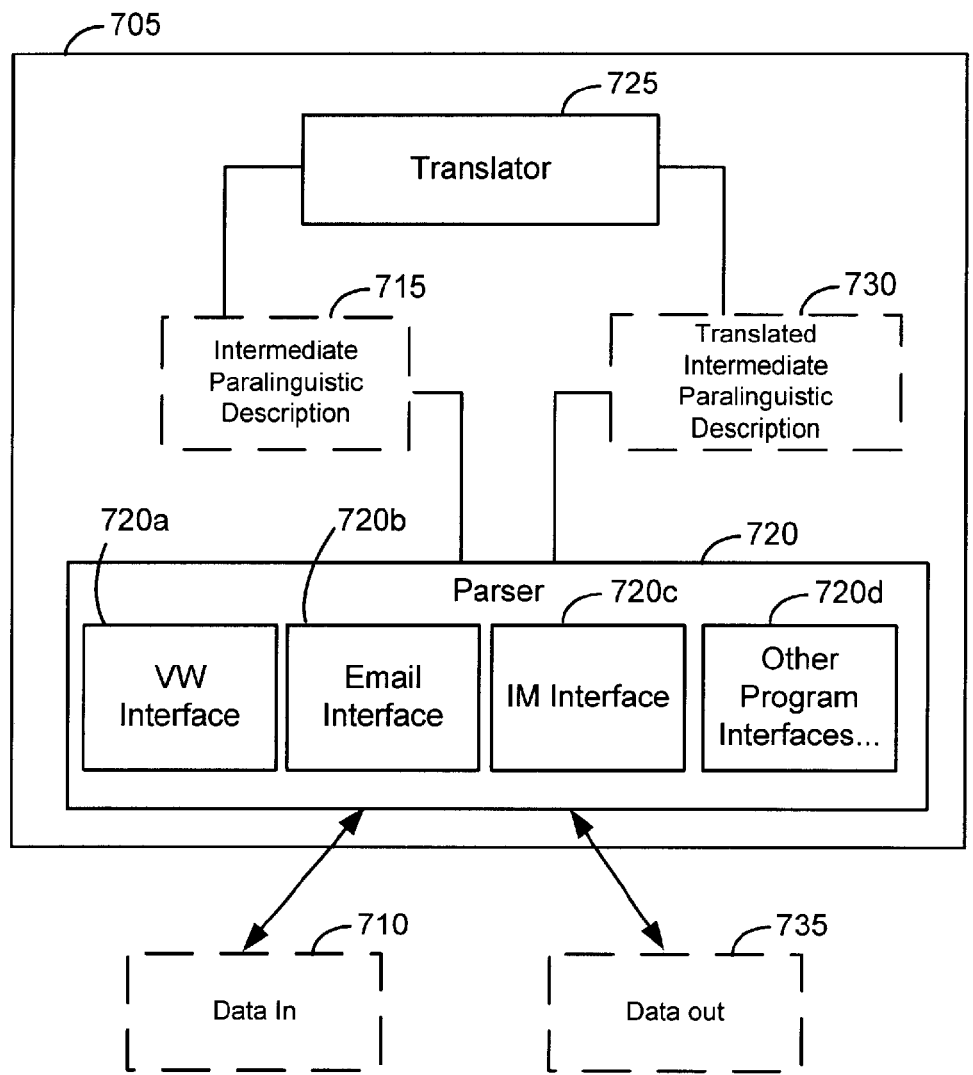
FIG. 7 is a block diagram of a paralinguistic translation server.

FIG. 7 illustrates a translation system 700 that includes an exemplary paralinguistic translation server 705. Paralinguistic translation server 705 is structured and arranged to receive, from a source, a first set of data 710 related to a first paralinguistic indicator that is configured to enable non-verbal communications between a source and a destination, wherein the source is one of an instant messaging system and a virtual world system and the destination is one of the textual instant messaging system and a virtual world system but differs from the source, Paralinguistic translation server 705 is also structured and arranged to translate the first set of data 710 related to the first paralinguistic indicator into a second set of data 735 related to a second paralinguistic indicator that is at least partially synonymous to the non-verbal communications associated with the first paralinguistic indicator, and to transmit the second set of data 735 to the destination.

In more detail, paralinguistic translation server 705 includes a parser 720 that is structured and arranged to perform parsing on data sets related to paralinguistic indicators. The parser 720 includes parsing interfaces 720*a*-720*d*. Parsing interfaces 720*a*-720*d* are capable of decoding data sets related to paralinguistic indicators from various instant messaging, email, or virtual world clients, and converting the decoded data sets into a common intermediate paralinguistic format. Alternatively or in addition, parsing interfaces 720*a*-720*d* may be used to convert data specified in the common intermediate paralinguistic format back into the specific formats used by the various instant messenger, email, or virtual world clients. Thus, the parser 720 may include interfaces 720*a*-720*d* for encoding or decoding data sets using a proprietary IM interface. Alternatively or in addition, the parser 720 may include interfaces for encoding or decoding data sets using the proprietary interfaces of different VW clients, such as Second Life.

Paralinguistic translation server 705 also includes a translator 725 that is structured and arranged to translate a set of data 710 related to the first paralinguistic indicator into a second set of data 735 related to a second paralinguistic indicator, such that the second paralinguistic indicator is at least partially synonymous to the first paralinguistic indicator.

Figure 8:
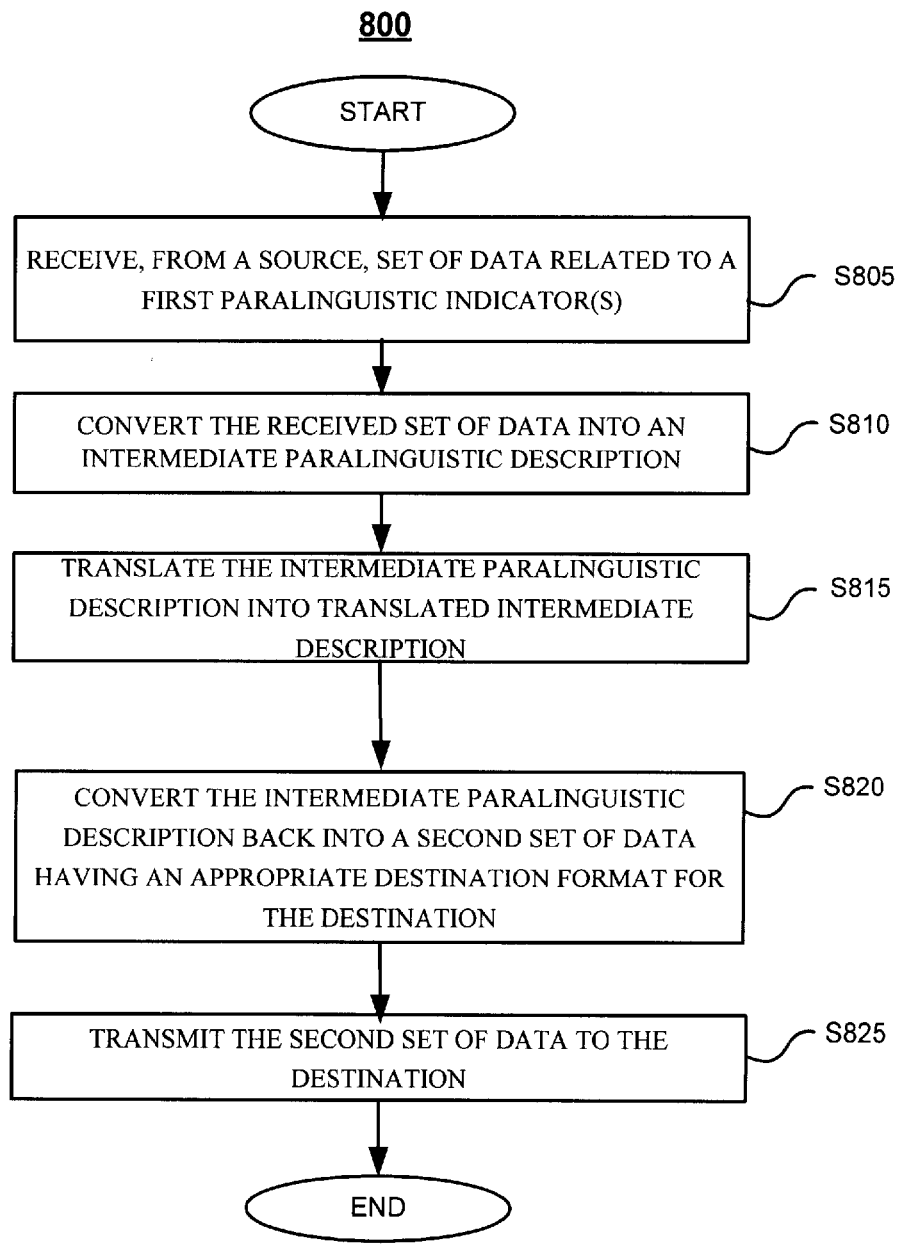
FIG. 8 is a flowchart of an exemplarily operation of a paralinguistic translation server.

FIG. 8 shows a flowchart 800 of an exemplarily operation of paralinguistic translation server 705 of FIG. 7. Paralinguistic translation server 705 receives, from a source, data set 710 related to a first paralinguistic indicator(s) (step 805). Data set 710 may be received, for example, from the VW server and thus, would describe paralinguistic indicators in the virtual world. Data set 710 may also be received from the IM server, and would then describe paralinguistic indicators in IM interface. Data set 710 may be specified in an Extensible Markup Language (XML), HTML, Python, the format used by the VW or IM clients, or any other open or proprietary format or scripting language. Data set 710 also may include a combination of text data, voice data, and video data.

Paralinguistic translation server 705 converts the received data 710 to an intermediate paralinguistic description (step 810). The conversion may use an intermediate paralinguistic description because protocols and formats used by different VW clients or clients are incompatible. Thus, a Yahoo instant messenger client and an AIM client may require different text triggers to elicit the same emoticon. Similarly, different virtual world clients also may use proprietary/incompatible formats related to the paralinguistic indicators. Therefore, paralinguistic translation server 705 may decode data sets expressed in different formats into the common format before proceeding with the actual translation. Operating on data sets in the common format enables a paralinguistic translation server 705 to translate the abstract meaning between paralinguistic indicators of different clients while avoiding additional complexity that may result from a requirement to operate in the particularities of the clients' data formats.

Paralinguistic translation server 705 may decode data set 710 into the intermediate paralinguistic description 715 using a parser 720. Intermediate paralinguistic description 715 may be expressed in an XML-based format. One illustrative example of an XML-based format for describing paralinguistic indicators is Emotion Annotation and Representation Language (EARL), currently in development by the W3 community. The XML-based format for describing paralinguistic indicators may include emotional tags for specifying emotions. Both simple and complex emotions may be specified. In addition, emotions may be grouped by categories, such as "negative and passive", "agitated," or "caring."

The XML-based format for describing paralinguistic indicators may be capable of describing a variety of emotional states by using emotional tags of varying complexity. A simpler emotional tag utilizes various attributes to specify a category, dimensions (e.g., intensity) and/or appraisals of a single emotional state. Emotional tags may include text, links to other XML nodes, or specify a time span using start and end times to define their scope.

In one implementation, an emotional tag may specify a homogenous emotion. For example, referring back to FIG. 6, the following XML tag may describe a simple angry emotion in the message 640:

<emotion category="anger">I AM SO ANGRY!!!</emotion>

On the other hand, a more complex emotional tag describes an emotion that is composed of several emotions. For example, complex emotions may be used in cases where two or more emotions co-occur, or situation where one emotion is masked by the simulation of another one. The table below specifies an exemplary XML schema for specifying complex emotions. Each complex emotion can have different intensity, modality, or probability. The intensity variable specifies the intensity of the emotion. The modality variable specifies how the emotion is expressed—e.g., the emotion may be expressed through speech, facial expressions, or specific body gestures. The probability variable assigns a probability to an event that a specific emotion will occur or is actually occurring. Other attributes of complex emotions, such as time durations for each sub-emotion, may be used.

```
<xsd:schema xmlns:xsd
    <xsd:simpleType name="modalityType">
        <xsd:enumeration value="voice"/>
        <xsd:enumeration value="text"/>
        <xsd:enumeration value="face"/>
        <xsd:enumeration value="body"/>
    </xsd:simpleType>
    <xsd:attribute name="modality" type="modalityType"
    use="optional"/>
    <xsd:attribute name="probability" type="xsd:float"
    use="optional"/>
    <xsd:attribute name="intensity" type="xsd:float" use="optional"/>
</xsd:schema>
```

For example, the following XML tag may describe a complex angry emotion expressed by the avatar 610 in FIG. 6:

```
<complex-emotion>
    <emotion category="anger" modality="face" intensity="0.5/>
    <emotion category="stress" modality="face" />
    <emotion category="anxiety" modality="body" />
</complex-emotion>
```

As can be seen from the above example, the described complex emotion not only takes into account the facial expressions 620 of the avatar 610, but also its various gesticulations, such as hand movements 630. As a result, a much more complete emotional snapshot may be conveyed for the avatar 610.

The paralinguistic translation server 705 next translates intermediate paralinguistic description 715 into translated intermediate description 730 (step 815). However, the translating process also may be performed directly on the data related to the paralinguistic indicators without first converting it to the intermediate paralinguistic format 715. For example, the paralinguistic translation server 705 may translate directly between paralinguistic indicators of the IM and the VW clients if these clients use the same or similar format for describing their paralinguistic indicators.

A variety of methods may be utilized at the paralinguistic translation server 705 for translating between paralinguistic indicators, whether they are expressed in the intermediate paralinguistic format 715 or not. For example, translation tables may be used. That is, direct translations may be identified from/to the paralinguistic indicators (or their intermediate descriptions) of the IM client to/from the paralinguistic indicators of the VW client.

For example, the paralinguistic indicators expressed in the intermediate format 715 may be first matched based on the category of emotions described in the schema shown in FIG. 9 (e.g., "happiness", "anger"). Next, the paralinguistic translation server selects a synonymous emotion appropriate for the IM client from the same emotional category. However, because the expressive capabilities of the IM client may be limited when compared to the expressive capabilities of the VW client, some complex emotions in the virtual world, especially the ones involving gesticulations or movements may not translate directly into the limited set of emotions available to the IM client. In such cases, the paralinguistic translation server 705 may convert (i.e., downgrade) the complex emotion from the virtual world to either a less complex emotion or a simple emotion for the IM client. In addition, the paralinguistic translation server 705 may add textual descriptions to the paralinguistic indicators to describe or supplement the translated paralinguistic indicators from the virtual world. In situations where the complexity of the emotion expressed in the virtual world is less than the complexity of the available emotion in the IM client, an upgrading conversion may be required. For example, additional parameters may be added to the translated paralinguistic indicator intended for the IM client.

Alternatively or in addition, more complex translation techniques may be used. For example, the paralinguistic indicators may be translated using XSLT (Extensible Stylesheet Language Transformations), by using neural networks that identify similar expressions and emotions (even if not identical), or by utilizing knowledge-based machine translation.

Two examples of translating paralinguistic indicators follow. The first example describes a translation of paralinguistic indicators sent from the IM client to the VW client. The second example describes a translation of paralinguistic indicators sent from the VW client to the IM client.

In the first example, an IM user (e.g., user 120a from FIG. 1) sends an angry message to the VW user (e.g., user operating client system 105c from FIG. 1). Specifically, the IM user 105a sends a message to the VW user operating client system 105c, which includes a ">:-<" trigger indicating an "absolutely livid!" emotion. The paralinguistic translation server 705 receives the instant message, decodes its contents using the IM interface 720c, and retrieves the data related to the paralinguistic indicator of the IM user 105a. In this example, the data includes a ">:-<" trigger, Parser 720 converts the received paralinguistic indicator to the intermediate paralinguistic format 715. For example, because the 'absolutely livid' emotion is more complex than a simple "mad" or "angry" emotion, the paralinguistic translation server 705 may convert "absolutely livid" to the following exemplarily complex emotion:

```
</complex-emotion>
    <emotion category="anger" modality="face" arousal="0.9"
    power="0.6/>
    <emotion category="agitation" modality="face"
    arousal="0.3" power="0.5/>
</complex-emotion>
```

The paralinguistic translation server 705 also adjusts numerical values of the parameters of the complex emotion, such that the complex emotion most closely matches the parameters of the original paralinguistic indicator. Next, the paralinguistic translation server translates the complex emotion expressed in the intermediate paralinguistic format 715 to a synonymous complex emotion 730 that would be appropriate in the virtual world, while taking into the account the visual capabilities of the virtual world. For example, because the avatars in the virtual world are capable of expressing not only facial expressions, but also gesticulations, the paralinguistic translation server may add additional parameters to the complex emotion, such as hand or head movements. Other various facial/physical expressions and actions may be added to fully capture the emotion in the virtual world. The resulting translation may look as the following:

```
</complex-emotion>
    <emotion category="anger" modality="face" arousal="0.9"
    power="0.6/>
    <emotion category="agitation" modality="face"
    arousal="0.3" power="0.5/>
    <emotion category="frustration" modality ="body"
    arousal="0.4" power="0.7/>
    <emotion category="confusion" modality="body"/>
</complex-emotion>
```

In the second example, VW user operating client system 105c communicates with the IM user 105a. For example, the VW user operating client system 105c places his avatar in an elated mood. In addition, the VW user operating client system 105c makes his avatar display various celebratory hand gestures, such as "high fives." The paralinguistic translation server 705 receives data 710, which specifies avatar's actions/mood in the virtual world and decodes data 710 by using the VW interface 720a. Using the previously described parsing process, the paralinguistic translation server 705 converts the decoded data from the VW client into the intermediate paralinguistic format 715. For example, avatars actions/mood/emotions may be converted to the following exemplarily complex emotion:

```
<complex-emotion>
    <emotion category="happy" modality="face" arousal="0.9"
    power="0.6/>
    <emotion category="elation" modality="face" arousal="0.5"
    power="0.5/>
    <emotion category=" excitement " modality="figure"
    power="0.2/>
</complex-emotion>
```

Subsequently, the paralinguistic translation server 705 translates the complex emotion of the virtual world to a synonymous complex emotion that would be appropriate for the instant messaging, while also taking into the account the visual capabilities of the IM client. For example, because the visual capabilities of the IM client are limited when compared to the visual capabilities of the VW client, some complex emotions in the virtual world, especially the ones involving gesticulations or movements may not translate directly into the limited set of emoticons available to the IM client. In such a case, the paralinguistic translation server may convert the complex emotion from the virtual world to either a less complex emotion or a simple emotion. Additionally or alternatively, the paralinguistic translation server 705 may add textual descriptions to the instant message to describe or supplement the translated paralinguistic indicators. For example, the paralinguistic translation server may add "avatar waiving hand+jumping around the purple fountain" text to the instant message to describe avatar's actions in the virtual world. The resulting translation of the virtual world's paralinguistic indicator may look as following:

<emotion category="happy"> avatar waiving hands+ jumping around </emotion>

In the next step, the translated complex emotion expressed as the intermediate paralinguistic description 730 is converted into a set of data 735 having an appropriate format for the destination (step 820). This may be accomplished by parser 720, which encodes the intermediate paralinguistic description 730 using the appropriate interface. Therefore, in the case of the first example, (IM to VW translation), parser 720 uses VW interface 720a to convert the intermediate paralinguistic description 730 into the VW format. In the case of the second example, (VW to IM translation), parser 720 uses IM interface 720c to convert the intermediate paralinguistic description 730 into the IM data. For instance, the IM interface 7200 encodes the above emotion as "^5" (high five) and ":-))" (very happy face) and inserts these text triggers into the instant message 735. Alternatively or additionally, the IM interface 720c may supplement the instant message 735 with textual descriptions of the actions taking place in the virtual world. For example, the textual description "randomuser is very happy, jumping around the purple fountain and waiving hands" is inserted in the text of the instant message 735.

Finally, encoded data 735 is transmitted to a destination (step 825). In case of the first example, the resulting data 735 related to the paralinguistic indicators, now in the VW format, is then transmitted to the VW server. Consequently, the avatar of the IM user in the virtual world shows an angry face while also displaying some frustrated hand gestures. In case of the second example, the resulting data specifying the translated paralinguistic indicators in the IM format 735 is transmitted to the IM server or the IM client. Consequently, the IM client displays the text of the transmitted instant message, along with the translated emoticons, on the IM user's desktop.

FIG. 9 illustrates an exemplary XML schema that may be used to represent mood information as paralinguistic indicators are translated between IM and VWs. The schema 900 supports a number of different emotions, which are grouped by emotional categories 905a-905g, such as "negative and forceful", "positive and lively," or "caring."

The schema 900 is capable of describing a variety of emotional states by using emotional tags of varying complexity. A simpler emotional tag utilizes various attributes to specify a category, dimensions (e.g., intensity) and/or appraisals of a single emotional state. Emotional tags may enclose text, links to other XML nodes, or specify a time span using start and end times to define their scope.

The paralinguistic translation server also may translate paralinguistic indicators by evaluating not only one indicator at a time, but also using an overall paralinguistic state of a user. That is, some users do not (or may not) abruptly transition between moods. For example, if a user is unhappy, the user may remain in an unhappy state of mind for some time. As a result, even if the user includes a "happy" emoticon in the instant message after thirty minutes of angry communications, it is possible that the happy emotion is highly transient or is not fully established. Thus, the paralinguistic translation server may track the user's paralinguistic state and utilize that state during the current or future translations of paralinguistic indicators. The paralinguistic state may be based on the context of current/previous textual communications as well as the previous values of the paralinguistic indicators collected over some time period. The XML-based values of emotional parameters discussed with respect to FIGS. 7, 8 and 9 may be used during calculations of the user's paralinguistic state. In one example, the paralinguistic translation server may keep a running average of paralinguistic values (e.g., category, modality, probability, intensity, etc.) to ensure that the user's translated emotions do not transition abruptly. Additionally or alternatively, the paralinguistic translation server may return the user's paralinguistic indicators back to the original state or an adjusted state if the paralinguistic translation server determines that user's emotional change was merely transient. Maintaining persistency in the user's paralinguistic state may allow the paralinguistic translation server to convey more realistic behavior on behalf of the IM user. A short example to illustrate the above concept follows.

An IM user is represented by an avatar in the virtual world. The paralinguistic translation server tracks the IM user's paralinguistic state. For example, based on the previous communications, the paralinguistic server determines that the IM user has been in an "angry" state for over 5 minutes. As a result, the IM user's avatar has been continuously placed in an "angry" state as well. Then, the IM user sends an instant message which includes a "smiley" emoticon. The paralinguistic translation server may detect that the "smiley" emoticon conflicts with the IM user's currently "angry" paralinguistic state. As a result, the paralinguistic translation server may translate the paralinguistic indicator (i.e., "smiley" emoticon) to a partially synonymous paralinguistic indicator in the virtual world (e.g., cause avatar to smile), but then return the IM user's avatar to the previous "angry" state. Additionally or alternatively, the paralinguistic translation server may adjust the IM user's state to "less angry." Thus, IM user's avatar would return to an angry or somewhat less angry state after smiling, but would not immediately transition to the "smiling" state.

In one implementation, translating a mood or expression may be performed using a hierarchy of moods to address inconsistencies between capabilities in the IM and VW systems. For example, a user in a VW system may be furious, which does not appear as a registered mood in the IM system. The paralinguistic translation server may recognize that "furious" is a subset of "angry", which the IM system does recognize. As a result, the paralinguistic translation server may translate the "furious" to "angry" in response to determining that the IM system does not recognize the value "furious" and that "furious" is a subset of "angry."

In addition to allowing an IM user to communicate with users of a virtual world client, as described above, a user may further interact with the virtual world environment using only a text-based communications client, such as, for example, an IM or email client. In this way, such a user, referred to as an IM user, may navigate the virtual world to cause an avatar that represents the IM user within the virtual world to move from one virtual world location to another. To do so, the IM user may execute commands, by typing them into an IM client window, that cause the avatar to move within the virtual world. The following shows some exemplary commands and associated actions.

| Command | Associated Action |
| --- | --- |
| <walk forwards, backwards, left, or right> | moves the avatar forwards, backwards, left, or right from the avatar's current location |
| <fly to location X> | causes the avatar to fly to a particular location identified in the command in place of the letter "X" |
| <teleport to location X> | causes the avatar to teleport to a particular location identified in the command in place of the letter "X" |
| <move proximate to/away from user Y> | moves the avatar next to, or away from, a particular other user identified by name in the command in place of the letter "Y" |

As the IM user navigates the virtual world, the avatar's current location may be monitored in order to provide the IM user with a textual description of the environment of a sub-portion of the virtual world corresponding to the avatar's current location in the virtual world. Such monitoring may be automatically performed when the avatar enters a new location, and/or an IM user may request such monitoring by executing a <look around> command.

The description of the environment may include a description of the physical environment (e.g., green grass, a blue house, a clothing store, and a red car), a description (or listing) of other users that are proximate to the avatar (e.g., users A, B, and C are nearby), and a description of activities taking place in the avatar's current location (e.g., user A is talking to user B, user C is walking her dog, a juggler is performing on the corner, and three users are playing a game of catch in the square).

In some instances, the IM user may not receive all possible environmental descriptions, proximate user descriptions, or activity descriptions that are determined to exist within the avatar's current location. For example, the IM user may be enabled to provide preference information related to the descriptions that are provided to the user. The user may provide preference information related to (1) a volume of descriptions to be provided to the user (e.g., provide up to 5 environmental descriptions for a particular location, provide up to 25 names of users who are proximate to the avatar, or provide a list of 10 activity descriptions per 15 minutes), (2) a type of descriptions to be provided to the user (e.g., only provide activity descriptions), and/or (3) a list of other users about whom descriptions are to be provided to the user (e.g., provide proximate user descriptions for users A, B, and C, or provide activity descriptions for users D and B).

In another example, the number of descriptions provided to an IM user may be limited based on a default, or user-defined, threshold number of descriptions. The threshold number of descriptions may be a total threshold (e.g., a total number of environmental, proximate user, and activity descriptions that may be provided to a user), or a different threshold number of descriptions may be determined on a per-description category basis (e.g., an environmental description threshold of 25 descriptions, and an activity description threshold of 15 descriptions).

In the case where the number of descriptions determined based on monitoring the avatar's current location substantially exceeds a particular threshold number of descriptions, an interestingness rating for each of the determined descriptions may be determined, and a sub-set of all current descriptions may be provided to the user based on the interestingness ratings. The interestingness rating may be, for example, based on an IM user's preferences (e.g., a user prefers activity descriptions to environmental descriptions), on a generic interestingness rating (e.g., activities involving two users are more interesting than those involving a single user), or on an interestingness rating provided by other users (e.g., a user who is juggling may assign a high interest rating to the juggling activity being performed by that user). Furthermore, particular objects, users, and activities may have default interestingness ratings. For example, on a scale of 1 to 100, with 100 representing a high interestingness rating, a tennis ball may have an interestingness rating of 15, while a two users kissing may have an interestingness rating of 75.

In some implementations, an interestingness rating may be used to determine which descriptions to provide to a user regardless of whether a threshold number of descriptions is exceeded. For example, an IM user may indicate that only descriptions associated with the top 10 interestingness rated objects, users, or activities should be provided for any particular location. In another example, the IM user may indicate that only descriptions associated with objects, users, or activities that exceed a particular interestingness rating threshold (e.g., above an interestingness rating of 65) should be provided to the IM user. Additionally, or alternatively, a system default may be set to determine how many, and how often, descriptions of different interestingness ratings should be provided to an IM user.

If an IM user wishes to receive more information about a particular description, the IM user may execute a <more detail about "description"> command. The IM user may identify the description about which the IM user wishes more information by identifying the description in the "description" portion of the command. A description may be identified using, for example, a description ID, which may be provided with the description, the entire description, or a keyword from the description. Additionally, or alternatively, the IM user may execute a <look closer at Z> command, where the user provides a name of another user, or a name of an object or a portion of a location, in the place of the "Z," where the IM user has previously received a description related to Z. For example, an IM user may receive a description that reads "randomuser is singing." To receive more information about this description, such as the name of the song that randomuser is singing or where randomuser is located, the IM user may execute the command <more detail about "singing"> or the command <look closer at "randomuser">. In response to the <more detail . . . > or <look closer . . . > command, the user may be provided with a description that indicates "randomuser is singing the song "Love Me Do" by the Beatles" or a description that indicates "randomuser is singing from the far street corner."

As described above with respect to FIG. 2, the IM system 200 presents a user with an IM user interface 205 that includes text box 210 that displays representations 215 of the user's contacts in a co-user list. An IM user may manually add or remove contacts from the co-user list. However, the co-user list also may be automatically configured based on navigation of the virtual world by the IM user and interaction with other users within the virtual world.

For example, a first user (e.g., an IM user) may navigate the virtual world using an IM client application as described above. An avatar that represents a second user (e.g., a user that is interacting with the virtual world using a virtual world client, a text-based client, or some other means) is detected as being located proximate to the first user. The IM client may determine if the second user is already included in a co-user list associated with the first user. If so, the IM client may enable the first user to begin a communications session with the second user. If not, the IM client may determine whether to add the second user to the co-user list associated with the first user.

To determine whether to add a particular user to a co-user list, one or more attributes associated with the particular user may be determined. There are two types of attributes: positive attributes and negative attributes. Users associated with positive attributes may be added automatically added to a co-user list associated with a first user when the first user and the positively attributed user are located proximate to one another. Users associated with negative attributes may not be added to such a co-user list, or, if the user is already included in the co-user list, may be removed, and blocked, from the co-user list. In some implementations, for a particular user that is already included in a co-user list, a communications session may be automatically initiated with the particular user only if the particular user is associated with a positive attribute.

Attributes may include activity that a user has engaged in previously, or is currently engaging in, as well as interactions between a user and other users. Examples of positive activity attributes include performing community service such as picking up litter, helping other users find a location or an object, and engaging in any non-negative activity. Examples of positive interaction attributes include hugging another avatar, smiling at another avatar, and shaking hands with another avatar.

Examples of negative activity attributes include engaging in destruction of property, littering, or shouting obscene or offensive language in a large group. Examples of negative interaction attributes include attempting, or engaging in, violent behavior towards another user, harassing another user, speaking to another user in an obscene, or offensive manner, or, in some situations, engaging in adult conduct in a public space.

Activities and interactions may be categorized as positive or negative attributes based on predetermined criteria set by, for example, a system administrator, or based on user preference information specific to an IM user.

It will be understood that various modifications may be made without departing from spirit and scope of the claims. For example, the operations may be performed in a different order and/or the components in the disclosed systems may be combined in a different manner and/or replaced or supplemented by other components. As an example, the paralinguistic translation server may be located on the IM server, VW server, or client computers. Other implementations are within the scope of the following claims.

What is claimed:

1. A computer-implemented method for enabling communications between users of a first environment and a second environment, the method comprising the following operations performed by at least one processor:
    enabling a first user to navigate the first environment by controlling an avatar representing the first user;
    capturing a first paralinguistic indicator made by the first user, the first paralinguistic indicator representing a first emotion of a first complexity compatible with the first environment;
    translating the first paralinguistic indicator into a second paralinguistic indicator different from the first paralinguistic, wherein the second paralinguistic indicator is communicated to a second user of the second environment and represents a second emotion of a second complexity different from the first complexity and is compatible with the second environment;
    wherein at least one of the first complexity and the second complexity is defined as the co-occurrence of two or more emotions.

2. The computer-implemented method of claim 1, the method further comprising the following operation performed by the at least one processor:
    providing the second user with a description of activities taking place in a sub-portion of the virtual world environment.

3. The computer-implemented method of claim 2, wherein the description comprises a textual description of at least one of:
    an environment associated with the sub-portion of the virtual world environment,
    proximity of other users to an avatar representing the second user in the sub-portion of the virtual world environment, or
    activities being performed by other users currently located in the sub-portion of the virtual world environment.

4. The computer-implemented method of claim 1, the method further comprising the following operations performed by the at least one processor:
    enabling the second user to provide preference information related to a description of activities taking place in a sub-portion of the virtual world environment; and
    providing the second user with the description of activities taking place in the sub-portion of the virtual world environment in accordance with the preference information.

5. The computer-implemented method of claim 4, wherein the preference information includes at least one of:
    a quantity of descriptions to be provided to the second user,
    a type of descriptions to be provided to the second user, or
    a list of other users about whom descriptions are to be provided to the second user.

6. A system that enables users of a first environment to interact with a second environment, the system comprising:
    a memory configured to store instructions;
    a processor configured to execute the instructions to:
    enable a first user to navigate the first environment by controlling an avatar representing the first user;
    capture a first paralinguistic indicator made by the first user, the first paralinguistic indicator representing a first emotion of a first complexity compatible with the first environment;
    translate the first paralinguistic indicator into a second paralinguistic indicator different from the first paralinguistic indicator, wherein the second paralinguistic indicator is communicated to a second user of the second environment and represents a second emotion of a second complexity different from the first complexity and is compatible with the second environment;
    wherein at least one of the first complexity and the second complexity is defined as the co-occurrence of two or more emotions.

7. The system of claim 6, wherein the processor is further configured to execute the instructions to:
    access a collection of descriptions determined to be relevant to the second user;
    monitor a sub-portion of the virtual world environment corresponding to a current location of an avatar representing the second user in the virtual world environment;
    identify, from the collection of descriptions, a sub-set of descriptions based on monitoring the sub-portion of the virtual world environment and a threshold number; and
    provide the second user with the sub-set of descriptions.

8. The system of claim 7, wherein the processor is further configured to execute the instructions to:
    determine that a quantity associated with the collection of descriptions exceeds the threshold number;
    determine an interest rating for each description in the collection of descriptions; and
    provide the second user with the sub-set of the descriptions based on the interest ratings.

9. The system of claim 7, wherein the processor is further configured to execute the instructions to:
    determine that a quantity associated with the collection of descriptions exceeds the threshold number;
    determine an interest rating for each description in the collection of descriptions;
    access user interest preferences;
    compare the interest rating with at least one of the user interest preferences; and
    identify descriptions to be included in the sub-set of descriptions based on the comparison.

10. The system of claim 6, wherein the processor is further configured to execute the instructions to:
    receive, from a messaging interface of the instant messaging application, a detailed information request from the second user regarding a particular description provided to the second user;
    identify detailed information related to the particular description; and
    provide the second user with the detailed information related to the particular description.

11. The system of claim 6, wherein the processor is further configured to execute the instructions to:
    provide the second user with a description of activities taking place in a sub-portion of the virtual world environment.

12. The system of claim 11, wherein the description comprises a textual description of at least one of:
    an environment associated with the sub-portion of the virtual world environment,
    proximity of other users to an avatar representing the second user in the sub-portion of the virtual world environment, or
    activities being performed by other users currently located in the sub-portion of the virtual world environment.

13. The system of claim 6, wherein the processor is further configured to execute the instructions to:

enable the second user to provide preference information related to a description of activities taking place in a sub-portion of the virtual world environment; and provide the second user with the description of activities taking place in the sub-portion of the virtual world environment in accordance with the preference information.

14. The system of claim 13, wherein the preference information includes at least one of:
   a quantity of descriptions to be provided to the second user,
   a type of descriptions to be provided to the second user, or
   a list of other users about whom descriptions are to be provided to the second user.

15. A non-transitory computer-readable medium encoded with instructions, which when executed by a processor, cause the processor to perform operations comprising:
   enabling a first user to navigate a first environment by controlling an avatar representing the first user;
   capturing a first paralinguistic indicator made by the first user, the first paralinguistic indicator representing a first emotion of a first complexity compatible with the first environment;
   translating the first paralinguistic indicator into a second paralinguistic indicator different from the first paralinguistic indicator, wherein the second paralinguistic indicator is communicated to a second user of a second environment and represents a second emotion of a second complexity different from the first complexity and is compatible with the second environment;
   wherein at least one of the first complexity and the second complexity is defined as the co-occurrence of two or more emotions.

16. The non-transitory computer-readable medium of claim 15, the operations further comprising:
   providing the second user with a description of activities taking place in a sub-portion of the virtual world environment.

17. The non-transitory computer-readable medium of claim 16, wherein the description comprises a textual description of at least one of:
   an environment associated with the sub-portion of the virtual world environment,
   proximity of other users to an avatar representing the second user in the sub-portion of the virtual world environment, or
   activities being performed by other users currently located in the sub-portion of the virtual world environment.

18. The non-transitory computer-readable medium of claim 15, the operations further comprising:
   enabling the second user to provide preference information related to a description of activities taking place in a sub-portion of the virtual world environment; and
   providing the second user with the description of activities taking place in the sub-portion of the virtual world environment in accordance with the preference information.

19. The non-transitory computer-readable medium of claim 18, wherein the preference information includes at least one of:
   a quantity of descriptions to be provided to the second user,
   a type of descriptions to be provided to the second user, or
   a list of other users about whom descriptions are to be provided to the second user.

20. The non-transitory computer-readable medium of claim 15, wherein the first paralinguistic indicator is configured for non-verbal communications.

* * * * *